(12) United States Patent
Zhang et al.

(10) Patent No.: US 8,455,252 B2
(45) Date of Patent: Jun. 4, 2013

(54) MATERIALS AND METHODS FOR SENSITIZING MULTIDRUG RESISTANT CELLS

(75) Inventors: Jian-Ting Zhang, Carmel, IN (US); Jing Qi, Carmel, IN (US); Hui Peng, Beijin (CN); Zizheng Dong, Carmel, IN (US)

(73) Assignee: Indiana University Research and Technology Corp., Indianapolis, IN (US)

( * ) Notice: Subject to any disclaimer, the term of this patent is extended or adjusted under 35 U.S.C. 154(b) by 0 days.

(21) Appl. No.: 13/125,530

(22) PCT Filed: Oct. 24, 2009

(86) PCT No.: PCT/US2009/061980
§ 371 (c)(1),
(2), (4) Date: Jul. 25, 2011

(87) PCT Pub. No.: WO2010/048603
PCT Pub. Date: Apr. 29, 2010

(65) Prior Publication Data
US 2011/0301108 A1 Dec. 8, 2011

Related U.S. Application Data

(60) Provisional application No. 61/108,161, filed on Oct. 24, 2008.

(51) Int. Cl.
*A61K 31/425* (2006.01)
*A61K 31/54* (2006.01)

(52) U.S. Cl.
USPC .......... 435/375; 514/34; 514/232.5; 514/245; 514/391; 514/454; 514/241; 514/26; 514/250; 514/341; 514/418; 544/197; 544/205; 544/206; 544/207; 544/216

(58) Field of Classification Search
USPC ................. 435/375; 514/34, 232.5, 245, 391, 514/454, 241, 26, 250, 341, 418; 544/197, 544/205, 206, 207, 216
See application file for complete search history.

(56) References Cited

U.S. PATENT DOCUMENTS 6,943,161 B2  9/2005  Erickson et al.

OTHER PUBLICATIONS

Ozvegy-Laczka et al., High Affinity Interaction of Tyrosine Kinase Inhibitors with the ABCG2 Multidrug Transporter. Molecular Pharmacology, 2004. vol. 65, pp. 1485-1495.
Hazai et al. Homology Modeling of Breast Cancer Resistance Protein (ABCG2). J. Structural Bio, Apr. 2008. vol. 162(1), pp. 63-74.
Shigemura et al., Autologous Transplantation of Adipose Tissue-Derived Stromal Cells Ameliorates Pulmonary Emphysema, American Journal of Transplantation, 2006. vol. 6, pp. 2592-2600.
Ishizawa et al., Bone Marrow-Derived Cells Contribute to Lung Regeneration After Elastase-Induced Pulmonary Emphysema, FEBS Letters 556, 249-252 (2004).

*Primary Examiner* — Savitha Rao
(74) *Attorney, Agent, or Firm* — Faegre Baker Daniels LLP

(57) ABSTRACT

Disclosed herein are materials and methods for sensitizing multidrug resistant cancer cells that express ABCG2 and related proteins members of a family of ATP-binding transporter superfamily that mediate drug efflux found in some types of multidrug resistant cancer cells. A series of compounds, including (N-(4-chlorophenyl)-2-[(6-{[4,6-di(4-morpholinyl)-1,3,5-tri-azin-2-yl]amino}-1,3-benzothiazol-2-yl)sulfanyl]acetamide), specifically inhibits ABCG2 and can be used to boost the bio-avail-ability of one or more effective cancer killing drugs, making it possible to use certain widely used chemotherapeutic reagent to treat multidrug resistance cancers. Using these compounds in combination with chemotherapeutic drugs that are substrates for ABCG2 and related proteins may also find utility in treating cancer cells that are not currently identified as multi-drug resistant. Additionally, these compounds appear to accelerate the inter-cellular degradation of ABCG2 and related proteins. They are not toxic to animals at levels at which they effect the activity of ABCG2 expressed in multi-drug resistant cancer lines.

12 Claims, 20 Drawing Sheets

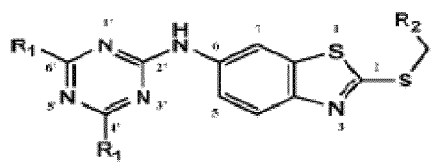
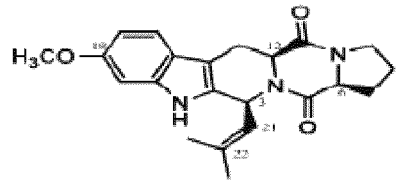

Basic structure of PZ-39        Fumitremorgin C

| Cmpd | R1 | R2 | Fluorescence Intensity | Cmpd | R1 | R2 | Fluorescence Intensity |
|---|---|---|---|---|---|---|---|
| A-1 | pyrrolidinyl | COOC$_2$H$_5$ | 154±13 | C-5 | morpholinyl | OC-NH-tetrahydrofuryl | 213±19 |
| A-2 | pyrrolidinyl | OC-NH-phenyl | 179±6 | C-6 | morpholinyl | HN-OC-tBu | 283±22 |
| A-3 | pyrrolidinyl | OC-NH-phenyl | 210±14 | C-7 | morpholinyl | CN | 246±11 |
| A-4 | pyrrolidinyl | OC-phenyl | 193±22 | C-8 | morpholinyl | COCH$_3$ | 242±18 |
| A-5 | pyrrolidinyl | OC-NH-CH$_2$-O-phenyl | 230±24 | D-1 | morpholinyl | OC-NH-phenyl-Cl | 266±7 |
| A-6 | pyrrolidinyl | OC-NH-CH$_2$-furyl | 197±16 | D-2 | morpholinyl | OC-NH-phenyl-CH$_3$ | 243±27 |
| A-7 | pyrrolidinyl | C$_2$H$_5$ | 133±12 | D-3 | morpholinyl | OC-NH-phenyl-F | 283±20 |
| A-8 | pyrrolidinyl | OCNH-tolyl | 155±21 | D-4 | morpholinyl | OC-NH-phenyl-CF$_3$ | 277±18 |
| B-1 | piperidinyl | COOCH$_3$ | 143±18 | D-5 | morpholinyl | OC-NH-phenyl-Cl | 282±12 |
| B-2 | piperidinyl | OC-NH-O-phenyl | 148±10 | D-6 | morpholinyl | OC-NH-phenyl-OEt | 244±29 |
| B-3 | piperidinyl | N-indazolyl | 178±20 | D-7 | morpholinyl | OC-NH-phenyl-CH$_3$ | 280±29 |
| C-1 | morpholinyl | COOC$_2$H$_5$ | 167±23 | D-8 | morpholinyl | OC-NH-xylyl | 225±7 |
| C-2 | morpholinyl | OC-NH-CH$_2$-O-phenyl | 217±27 | D-9 | morpholinyl | OC-NH-phenyl | 276±23 |
| C-3 | morpholinyl | OC-N-dibenzazepinyl | 215±24 | E-1 | phenyl-NH | O-phenyl-O-NH | 251±3 |
| C-4 | morpholinyl | OC-morpholinyl | 190±12 | E-2 | phenyl-NH | N-pyrrolidinyl-C=O | 313±21 |

MATERIALS AND METHODS FOR SENSITIZING MULTIDRUG RESISTANT CELLS

CROSS-REFERENCE TO RELATED APPLICATION

This application is a National Stage filing of International Application Serial No. PCT/US2009/061980, filed Oct. 24, 2009 and designating the United States, which claims priority to U.S. Provisional Application Ser. No. 61/108,161 filed Oct. 24, 2008, the disclosures of which are expressly incorporated herein by reference.

STATEMENT REGARDING FEDERALLY SPONSORED RESEARCH OR DEVELOPMENT

This invention was made with government support under CA120221 awarded by the National Institutes of Health. The United States Government has certain rights in the invention.

STATEMENT OF GOVERNMENTAL RIGHTS

Part of the development of this invention was made with government support from the National Institute of Health (NIH) under grant number CA120221. The U.S. government has certain rights in the invention.

FIELD OF INVENTION

This disclosure is related to materials and methods for sensitizing multidrug resistant cancer cells to various chemotherapeutic reagents by supply compounds that reduce the activity of various ATP binding cassette (ABC) transporters.

BACKGROUND

Multidrug resistance (MDR) is a major problem in the successful treatment of cancers. Over-expression of some members of the ABC (ATP-binding cassette) transporter super family has been suggested as a cause of MDR. One of the members of this family is ABCG2 which is thought to exist in the cell and functions as homo-oligomers of 8-12 subunits[1-3]. ABCG2 has also been implicated as playing a role in protecting cancer stem cells from chemotherapy drugs, resulting in drug resistance and the failure of cancer chemotherapy. Anticancer drug substrates of ABCG2 include, but are not limited to, such commonly used anticancer drugs such as: doxorubicin (8S,10S)-10-(4-amino-5-hydroxy-6-methyl-tetrahydro-2H-pyran-2-yloxy)-6,8,11-trihydroxy-8-(2-hydroxyacetyl)-1-methoxy-7,8,9,10-tetrahydrotetracene-5,12-dione) sold under the trade name Adriamycin; mitoxantrone (1,4-dihydroxy-5,8-bis[2-(2-hydroxyethylamino) ethylamino]-anthracene-9,10-dione); and topotecan ((S)-10-[(dimethylamino)methyl]-4-ethyl-4,9-dihydroxy-1H-pyrano[3',4':6,7]indolizino[1,2-b]quinoline-3,14(4H,12H)-dione monohydrochloride) sold under the trade name Hycamtin. Indeed, recent clinical studies have shown that over-expression of ABCG2 in both adult and childhood leukaemia correlates very well with a poor prognosis for the disease.[4] Knocking out ABCG2 activity appeared to have no readily apparent adverse effects on the development, biochemistry, and life of mice with this condition. Accordingly, inhibiting or reducing the activity of ABCG2 is unlikely to cause any serious side effects provided that the inhibitor is specific for ABCG2. This makes ABCG2 an ideal target for development of chemo-sensitizing agents for better treatment of drug resistant cancers.

Compared with the well-known drug resistance-causing ABC transporters such as ABCB1 (MDR1/Pgp) and ABCC1 (MRP1), ABCG2 was discovered relatively recently and, thus, few specific inhibitors of ABCG2 have been reported. One of the best known specific ABCG2 inhibitors is the potent mycotoxin Fumitremorgin C (FTC) secreted by *Aspergillus fumigatus*. However, the neurotoxicity of FTC limits its therapeutic potential. Analogues of FTC that exhibit lower toxicity than FTC have been developed including such compounds as Ko132 and Ko143[5]; the present inventors are unaware of any clinical trials exhibiting the efficacy of these molecules. Other inhibitors of ABCG2 have also been reported.[6,7] However, some of these reagents, such as GF120918, appear to lack specificity due to their effect on ABCB1 and/or ABCC1.[8,9] Clearly then, there is a need for more specific ABCG2 inhibitors to better treat drug resistant cancers. Aspects of the current invention seek to address the need discussed above.

SUMMARY

Disclosed herein are compounds and methods for sensitizing multidrug resistant cancer cells to chemotherapeutic drugs. Some methods comprise the steps of: obtaining a compound that effectively inhibits ABCG2; obtaining a chemotherapeutic drug that is a substrate ABCG2 or similar transporter, wherein the drug exhibits cell killing ability in the absence of high ABCG2 activity; and applying said compound and the drug to a MDR cell, wherein the cell expresses ABCG2. In some embodiments the ABCG2 inhibitor may exhibit mixed type inhibitor kinetics, and in some embodiments the compound may accelerate the lysosome-dependant degradation of ABCG2. In some embodiments, the compound comprises a benzothiazole linked to a traizine ring backbone having the following formula:

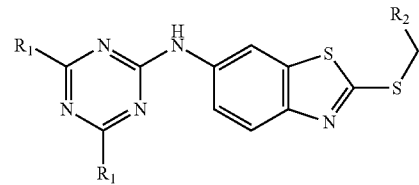

wherein, $R_1$ is selected from a group consisting of:

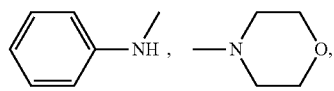

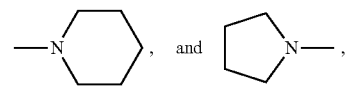

and R₂ is selected from a group consisting of

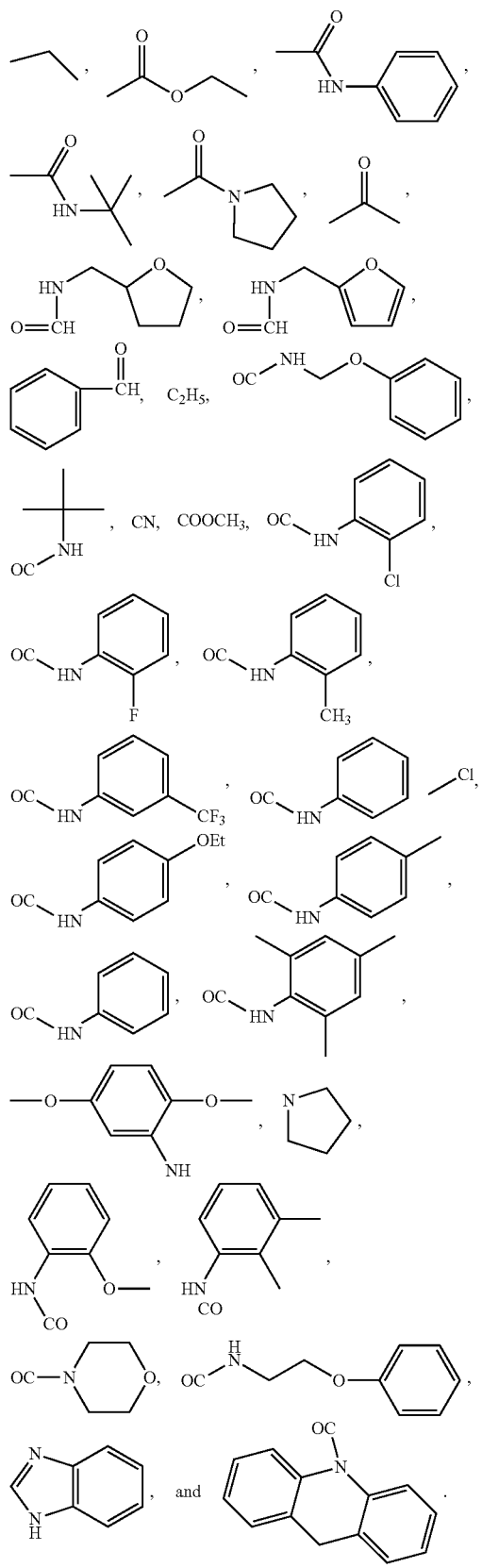

In other embodiments, the compound used to sensitize MDR cells has the following structure:

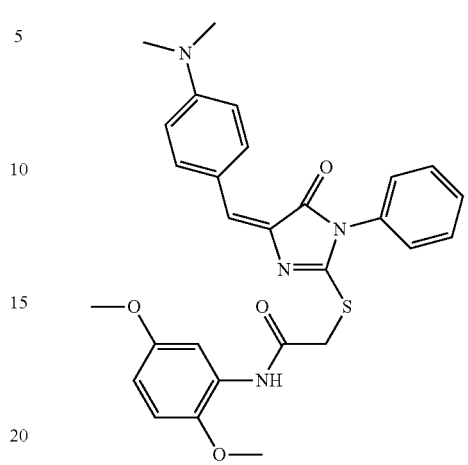

Some aspects of the invention include methods for overcoming multidrug resistance in cancer chemotherapy, comprising the steps of: providing a compound that inhibits ABCG2, wherein said compound comprises a benzothiazole linked to a traizine ring backbone as follows:

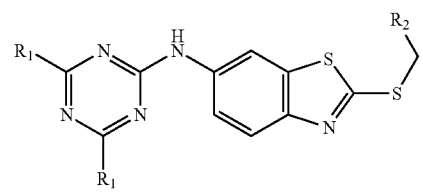

wherein, R₁ is selected from a group consisting of:

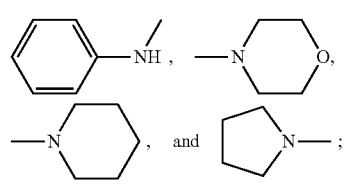

and
R₂ is selected from a group consisting of:

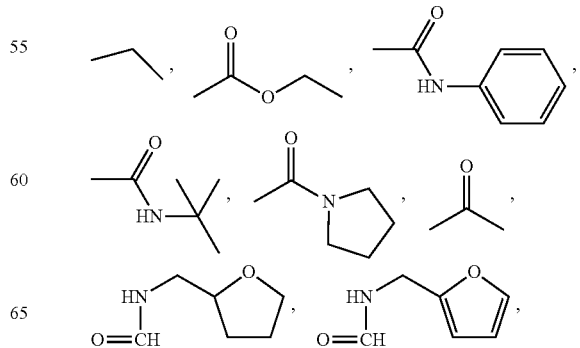

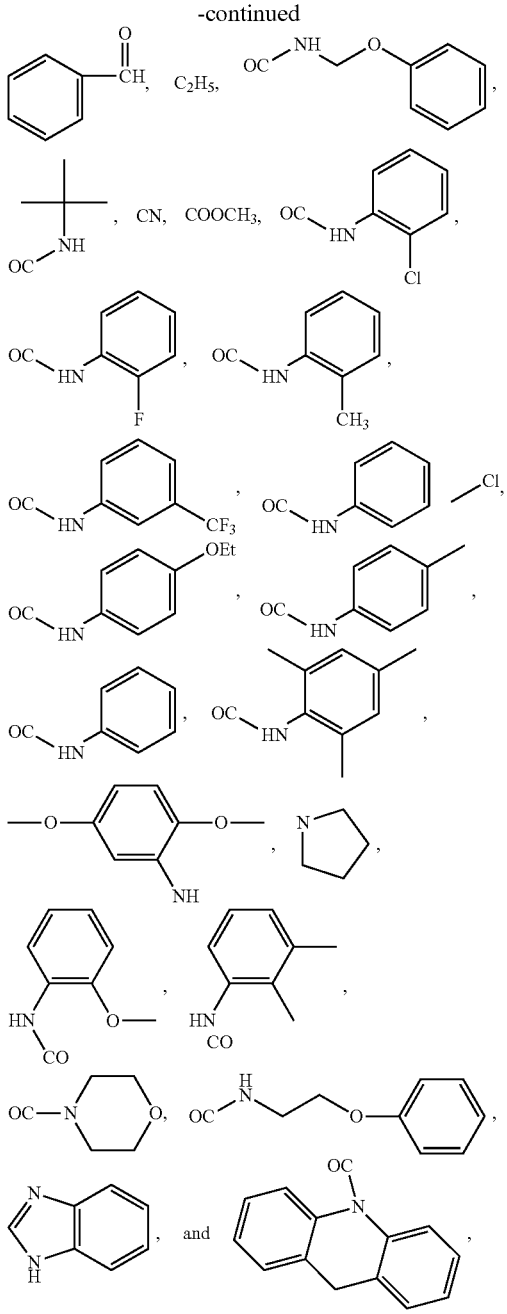

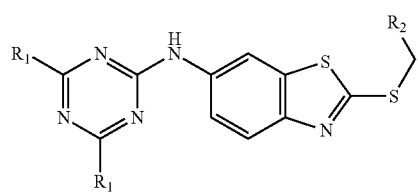

or a pharmaceutically effective salt thereof; obtaining a chemotherapeutic reagent, wherein the reagent is transported by an ABCG2 transport protein; and contacting said compound and the reagent with a multidrug resistance cancer cell, wherein said cell expresses ABCG2. In some embodiments the compound that inhibits ABCG2 is PZ-39. In still other embodiments the compound that inhibits ABCG2 is PZ-38. In some embodiments the amount of ABCG2 inhibitor used is on the order of 45 nM or less. In some embodiments the chemotherapeutic reagent is an anthracycline antibiotic, and in some embodiments the anthracycline antibiotic is adriamycin.

In still other embodiments the chemotherapeutic reagent is an anthracenedione, in some embodiments the anthracenedione is mitoxantrone. In other embodiments the chemotherapeutic reagent is a topoisomerase I inhibitor in some embodiments the topoisomerase I inhibitor is topotecan while in other embodiments it is camptothecin.

Still other aspects of the invention include methods for reducing the level of ABCG2 in a cell, comprising the steps of: providing a compound that reduces the level of ABCG2 in a cell, wherein said compound, or a pharmaceutically acceptable salt thereof, is selected from the group of compounds consisting of:

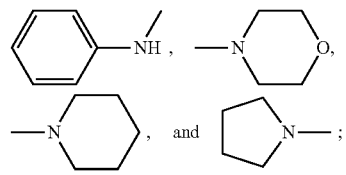

wherein, $R_1$ is selected from a group consisting of:

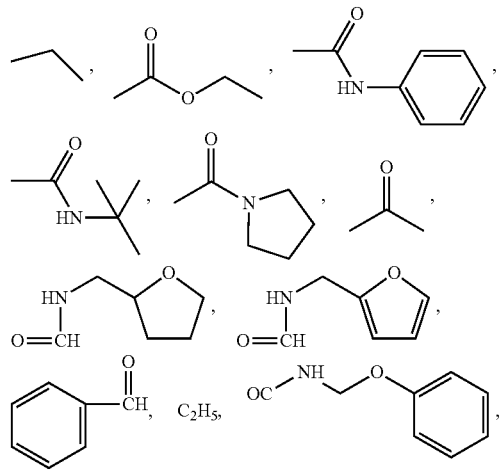

and
$R_2$ is selected from a group consisting of:

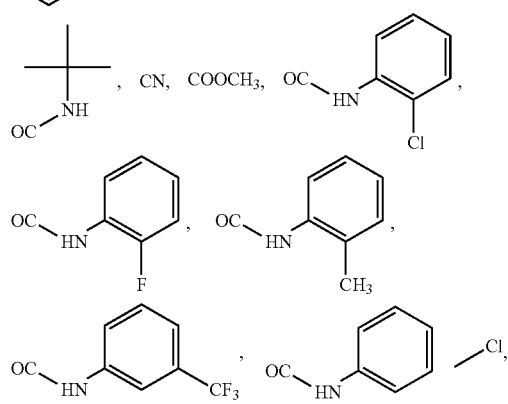

-continued

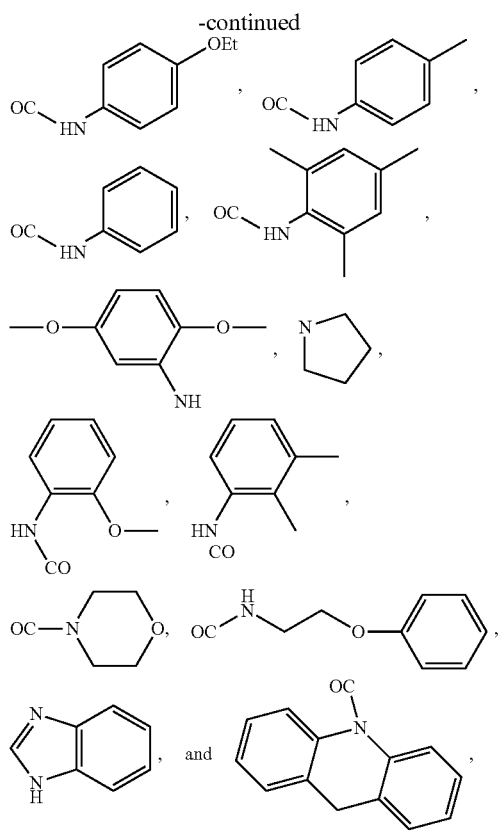

and contacting said compound with a cell, wherein the cell expresses ABCG2. In some embodiments the compound that inhibits ABCG2 is PZ-39 while in still other embodiments the compound that inhibits ABCG2 is PZ-38. In some embodiments the amount of ABCG2 inhibitor used is on the order of 45 nM or less.

Yet another aspect of the invention includes methods of treating a patient, comprising the steps of: providing a compound that inhibits ABCG2, wherein said compound or a pharmaceutically acceptable salt thereof, is selected from the group of compounds consisting of:

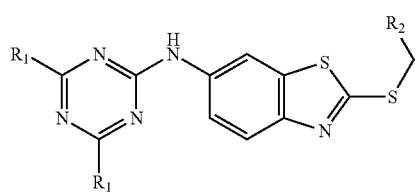

wherein, $R_1$ is selected from a group consisting of:

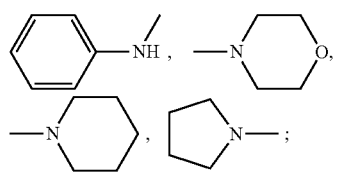

and $R_2$ is selected from a group consisting of:

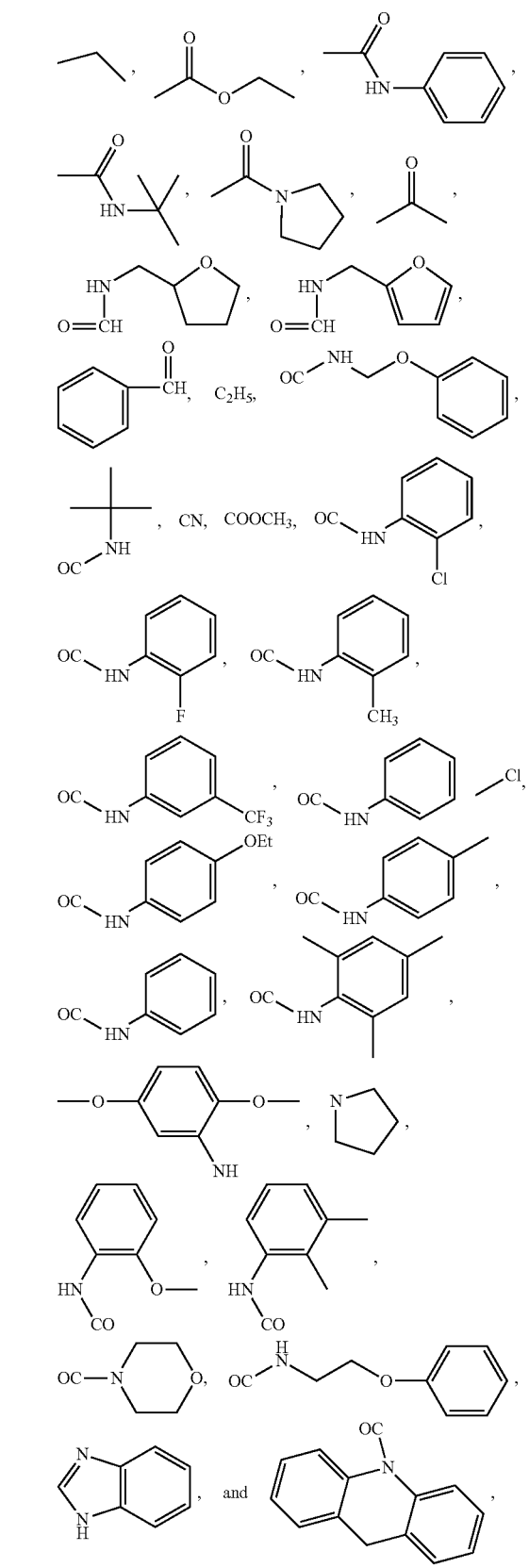

supplying at least one chemotherapeutic reagent or a pharmaceutically acceptable salt thereof, wherein the reagent is a substrate for ABCG2; and dosing a patient with a therapeutically effective amount of at least one of the compounds and at least one of the chemotherapeutic reagents.

Still other embodiments include methods of treating a patient, inhibiting ABCG2 and ABCG2 like proteins and/or treating a multi-drug resistant cell line, comprising the steps of: providing a compound that inhibits ABCG2, wherein said compound or a pharmaceutically acceptable salt thereof, is selected from the group of compounds consisting of:

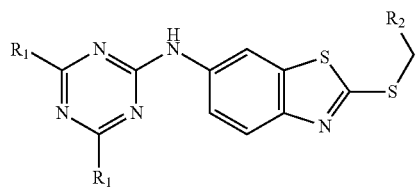

wherein, $R_1$ is selected from a group consisting of:

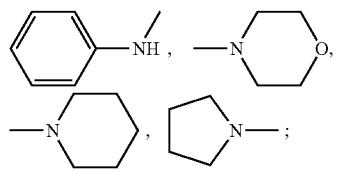

and $R_2$ is selected from a group consisting of:

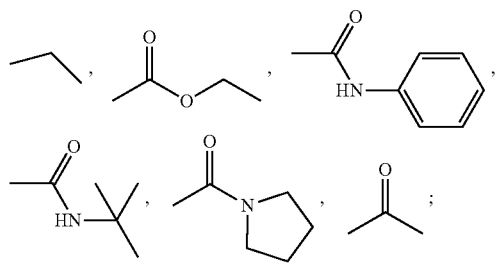

supplying at least one chemotherapeutic reagent or a pharmaceutically acceptable salt thereof, wherein the reagent is a substrate for ABCG2; and dosing a patient with a therapeutically effective amount of at least one of the compounds and at least one of the chemotherapeutic reagents.

In some embodiments the compound that inhibits ABCG2 is PZ-39, while in still other embodiment the compound that inhibits ABCG2 is PZ-38. In some embodiments the amount of ABCG2 inhibitor administered to the patient is on the order of 45 nM or less. In some embodiments the chemotherapeutic reagent is an anthracyclkine antibiotic. In some embodiments it is adriamycin. In still other embodiments chemotherapeutic reagent is an anthracenedione. In some embodiments the anthracenedione is mitoxantrone. In yet other embodiments the chemotherapeutic reagent is a topoisomerase I inhibitor. In some embodiments the topoisomerase I inhibitor is either topotecan camptothecin. In some embodiments a dose on the order of about 45 µg ml$^{-1}$ or less is administered to a patient in order to reduce ABCG2 activity.

Still other embodiments include using any of the compounds and analogues and derivatives thereof disclosed herein to treat, diagnose, and/or study cells that are multi-drug resistant and proteins such as ABCG2 and similar proteins that involved in conferring drug resistance on various cells, including cancer cells.

In some embodiments various chemotherapeutic reagents and various drug efflux inhibitors, including those disclosed and implied herein, are used in combination to treat patients, study and/or diagnose disease or normal cell physiology. Chemotherapeutic reagents that can be used in combination with the ABCG2 inhibits disclosed herein may be administered to patients at levels consistent with current dosing guidelines known in the art or in some instances at lower levels as well. Various embodiments also include using pharmaceutically acceptable salts of the various chemotherapeutic reagents and ABCG2 inhibitors that can be used to treat patients or conduct various tests. All of the compounds disclosed herein, their analogues and the various therapeutic compounds including chemotherapeutic drugs can also be formulated with various carriers, preservatives, solubilizing agents, excipients, and the like as are know in the art.

These and other features, aspects and advantages of the present invention may be better understood with reference to the following non-limiting schemes, formulas, figures, drawings and description.

BRIEF DESCRIPTION OF FIGURES

FIG. 6A. Table illustrating the core structure of molecules such as PZ-39 and various substitutes.

Figure 1:
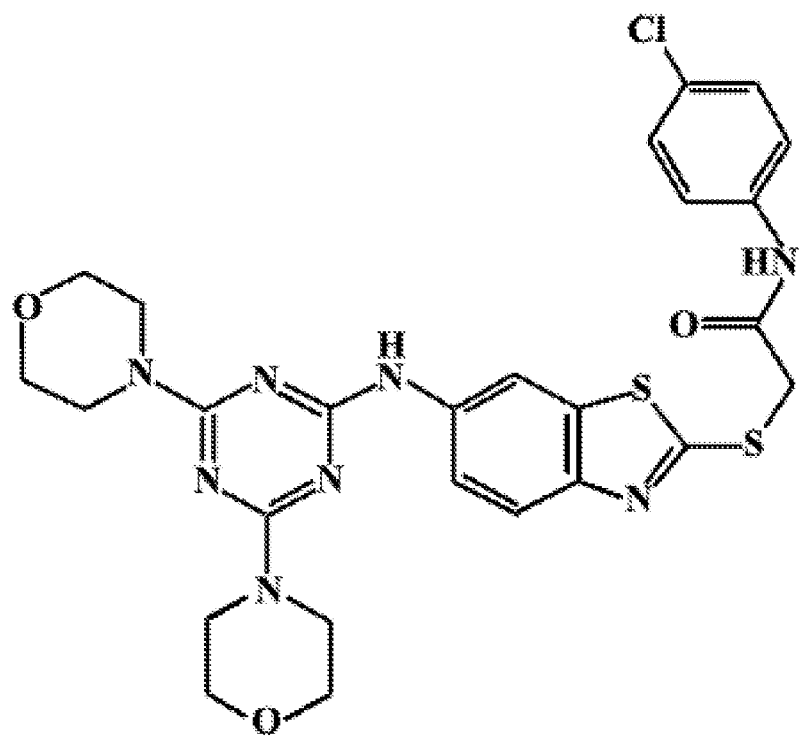
FIG. 1. Chemical structure of PZ-39, (N-(4-chlorophenyl)-2-[(6-{[4,6-di(4-morpholinyl)-1,3,5-triazin-2-yl]amino}-1,3-benzothiazol-2-yl)sulfanyl]acetamide); this molecule includes a benzothiazole linked to a triazine ring backbone.

Table 1: Potency index of PZ-39 in sensitizing drug resistance of HEK293/ABCG2 cells: a.) MX=100 nM mitoxantrone which produces ~10% inhibition of growth ($IC_{10}$); b.) Potency Index=ratio of inhibitor $IC_{50}$ in the absence and presence of anticancer drug mitoxantrone at low concentration ($<IC_{10}$); and c.) PZ-39 has no measurable cytotoxicity within the concentration range used and its $IC_{50}$ value was estimated to be bigger than that of FTC which is ~25 μM.

Table 2: Sensitization index of PZ-39 in HEK293/ABCG2 cells: a.) SI=sensitization index, determined by dividing $IC_{50}$ of mitoxantrone in the presence of inhibitors by $IC_{50}$ of mitoxantrone in the presence of DMSO vehicle.

DETAILED DESCRIPTION

While the concept of the present disclosure are illustrated and described in detail in the drawings and the description herein, such an illustration and description are to be considered as exemplary and not restrictive in character, it being understood that only the illustrative embodiments are shown and described and that all changes and modifications that come within the spirit of the disclosure are desired to be protected.

As used herein, the terms "subject" or "patient" is intended to mean a human, or an animal, in need of a treatment. This subject can have, or be at risk of developing, a disease or condition.

The term "treating" or "treatment" of a disease includes: (1) preventing the disease, i.e., causing the clinical symptoms of the disease not to develop in a subject that may be or has been exposed to the disease or conditions that may cause the disease, or predisposed to the disease but does not yet experience or display symptoms of the disease, (2) inhibiting the disease, i.e., arresting or reducing the development of the disease or any of its clinical symptoms, or (3) relieving the disease, i.e., causing regression of the disease or any of its clinical symptoms.

The phrase, "therapeutically effective amount," is the amount of the compound of the invention that will reduce the severity and/or the frequency of a given disease. Reducing the severity and/or frequency of a given disease includes arresting or reversing the disease, as well as slowing down the progression of the disease.

Administration "in combination with" one or more further therapeutic agents includes simultaneous or concurrent administration and consecutive administration in any order of various therapeutic compounds.

As used herein, an "effective dosage amount" or a "therapeutically effective dose or amount" is an amount that provides a therapeutically effective amount of the compound when provided as a single dose, in multiple doses, or as a partial dose. Thus, an effective dosage amount of the active compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

Alternatively, a pharmaceutical composition in which two or more unit dosages, such as in tablets, capsules and the like, are required to administer an effective amount of the calcium receptor-active compound may be administered in less than an effective amount for one or more periods of time (e.g., a once-a-day administration, and a twice-a-day administration), for example to ascertain the effective dose for an individual subject, to desensitize an individual subject to potential side effects, to permit effective dosing readjustment or depletion of one or more other therapeutics administered to an individual subject, and/or the like.

Unless noted otherwise, the term 'about' means plus or minus 20 percent, e.g. 'about 1.0' encompasses a range of values from 0.8 to 1.2.

Some abbreviations used herein include the following: ABC, ATP-binding cassette; MDR, multidrug resistance; MX, mitoxantrone; HA, hemagglutinin; SRB, Sulforhodamine B; PMSF, phenylmethylsulfonyl fluoride; DMSO, dimethyl sulfoxide; PBS, phosphate-buffered saline; FTC, fumitremorgin C, and as noted throughout.

Some aspects of the invention disclosed herein comprise a potent inhibitor of human ABCG2, designated herein as PZ-39. This compound has therapeutic utility in that it can be used to sensitize drug resistant cancers to various chemotherapeutic drugs. The exemplary compound, PZ-39 includes a benzothiazole linked to a triazine ring backbone without being bound by any specific hyperaction. It appears to act in two modes: (1) mixed type inhibition of ABCG2's drug transport function and (2) accelerated lysosome-dependent degradation of ABCG2. PZ-39 alone does not appear to be overly cytotoxic; it has a value on the order of about $IC_{50}$>25 µM. However, it is a very potent sensitizer of multidrug resistance cancer cells that over-express the protein ABCG2. Additionally, the substitution of certain functional groups on the core structure of PZ-39 appears to increase the efficacy of the core molecule, illustrating that the core is a suitable template for the development of additional useful inhibitors of ABCG2 and related proteins.

ABCG2 inhibitors, such as PZ-39 and PZ-39-like compounds, have a better therapeutic profile than many compounds currently used to inhibit ABCG2. For example, PZ-39 is a much more potent inhibitor of ABCG2 than is FTC. In a drug accumulation assay, at 3.3 µM of PZ-39 inhibited ABCG2 as well as 10 µM FTC did. In a cell survival assay, 500 nM PZ-39 was able to sensitize ABCG2-mediated mitoxantrone resistance with an index of about 0.04, while FTC at the same concentration had a sensitization index of only about 0.26, about 7-fold less. PZ-39 also has very low intrinsic cytotoxicity in vitro (>25 µM), and its potency index is also much better than FTC's, 1923 to 76, respectively. The therapeutic index window for PZ-39 is relatively wide. Accordingly, PZ-39 constitutes an ideal chemo-sensitizer in that by itself it exhibits very low toxicity. In addition to its ability to inhibit ABCG2 activity, PZ-39 also appears to accelerate the lysosome-dependent degradation of ABCG2's. This second mode of action is quite unexpected and it dramatically increases PZ-39's efficacy as a reducer of ABCG2 activity. This mechanism may also help to "recycle" the PZ-39 in the cell, thereby increasing its effective concentration in the cell and further increasing its potency as a multidrug resistance inhibitor.

The two modes of actions exhibited by PZ-39 make it an especially promising ABCG2 inhibitor. In its first mode the reduction and/or inhibition of ABCG2 activity PZ-39 exhibits a mixed type of inhibition in drug uptake assays. One non-limiting explanation of this characteristic is that PZ-39 may interact with ABCG2 directly although it does not appear to compete directly with the binding of ether mitoxantrone or ATP. In its second mode of action, PZ-39 appears to lower the availability of ABCG2 in the cells. PZ-39 appears to accelerate the degradation of ABCG2, by lysosomes as evidenced by a dramatic decrease of ABCG2 protein level in cells exposed to PZ39. One non-limiting explanation of this wholly unexpected second mode of activity is that the binding of PZ-39 causes a conformational change in ABCG2, which then targets ABCG2 for degradation in lysosomes. It is interesting to note that the binding of FTC has been reported to cause ABCG2 conformational change in ABCG2, but FTC has not been reported to accelerate the degradation of ABCG2. Assuming the PZ-39 accelerates the degradation of ABCG2's by inducing a conformation change in the proteins, this finding suggests that the conformational changes induced by PZ-39 and FTC may be different. It has been found that the degradation of a cysteine mutant ABCG2 occurs via the proteosomes, whereas the normal degradation of wild-type ABCG2 occurs via lysosomes, with a half-life of ~37 hrs. It has also been reported that the agonist-induced degradation of $\beta_2$-adrenergic receptor is via the lysosome, possibly by enhanced endocytosis. One possible explanation, offered by way of explanation and not limitation, for these data is that the binding of PZ-39 to ABCG2 accelerates endocytosis and the trafficking of cell surface thereby positioning ABCG2 into the lysosome for degradation.

Also disclosed herein are the results of testing certain derivatives of PZ-39 that include various functional groups identified in a series of 29 derivative compounds in a structural activity relationship analysis for their ability to sensitize drug resistance cells to treatment in some forms of chemotherapy. These derivatives share a common backbone comprising a benzothiazole linked to a traizine ring backbone, two identical $R_1$ groups, and one $R_2$ group as illustrated in FIG. 6A. The most active derivatives in this group appear to inhibit ABCG2 on about the same order of magnitude as does PZ 39. Generally, $R_1$ substitutions at positions 4' and 6' had the following order of potency: phenylamino>morpholine>piperidine≈pyrrolidine. Substitution at the $R_2$ position also significantly affects potency with an order of N-t-butylacetamide≈N-phenylacetamide>N-furanacetamide>acetate. A compound with a phenylamino group at $R_1$ and an N-t-butylacetamide at $R_2$ position will likely further improve the inhibitory activity of the core compound.

Figure 11:
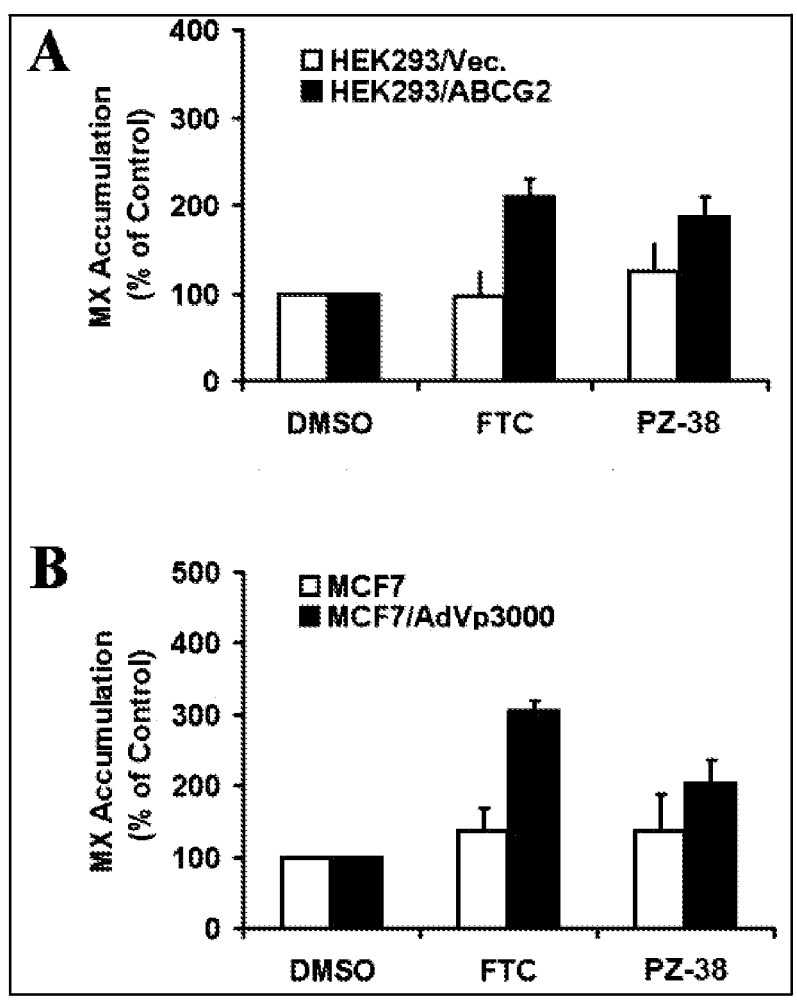
FIG. 11A. Bar graph illustrating the accumulation of mitoxantrone as a % of the control on either HEK293/VEC cells (open) or ABCG2-transfected HEK293 cells (closed); assays were run on cells exposed to each of the following conditions DMSO, 3 μM FTC or 3.8 μM PZ-38.
FIG. 11B. Bar graph illustrating the accumulation of mitoxantrone as a % of the control on either MCF7 cells (open) or MCF7/AdVp3000 cells (closed); assays were run on cells exposed to each of the following conditions DMSO, 3 μM FTC or 3.8 μM PZ-38.

Also disclosed herein is a second compound designated as PZ 38 which also inhibits ABCG2. PZ-38 may be used to sensitizing multidrug resistance cells to chemotherapeutic compounds. PZ-38 inhibits ABCG2-mediated mitoxantrone transport. As shown in FIGS. 11A and 11B, PZ-38 inhibited ABCG2-mediated drug efflux in ABCG2-transfected HEK293 cells (A) and drug resistant MCF7/AdVp3000 cells (B) better than DMSO alone and similar to the ABCG2 inhibitor FTC. The data are shown as mean±SD from three independent experiments. However, in these experiments PZ-38 had no measurable effect on drug accumulation in the control MCF7 and vector-transfected HEK293 cells that do not express ABCG2 one possible explanation for these results is that PZ-38 is specific for ABCG2. It should be noted that 3.8 µM PZ-38 had about the same effect as 3 µM FTC, suggesting that PZ-38 may be only as potent as, or perhaps somewhat less potent than FTC.

Materials and Methods

Materials. Monoclonal antibody BXP-21 against ABCG2, anti-Myc and anti-HA antibodies were obtained from ID Labs, Cell Signaling, and Roche, respectively. Biotin-conjugated 5D3 antibody and Phycoerythrin-Streptavidin conjugates were from eBiosciences. All electrophoresis reagents, protein concentration assay kit, precast polyacrylamide gradient gels and polyvinylidene difluoride membranes were purchased from Bio-Rad. FTC, Adriamycin, mitoxantrone, DTT, Sulforhodamine B (SRB), and Triton X-100 were obtained from Sigma. Protein-G PLUS-Agarose and SYBR Green PCR Master Mix were from Santa Cruz Biotechnology and Applied Biosystems, respectively. LipofectAMINE Plus and G418 were obtained from Invitrogen. Cell culture medium IMEM, DMEM, and [$^3$H]mitoxantrone were from BioSource International, Media Tech., and Moravek Biochemical, respectively. PZ-39 and all its derivatives were obtained from SPECS (Wakefield, R.I., USA). All other chemicals were of molecular biology grade and obtained from Sigma or Fisher Scientific.

Cell culture, lysate, and membrane preparations. Human breast cancer cell line MCF7 and its derivative lines BC19 and MCF7/AdVp3000, HEK293/ABCC1, HEK293/vector, HEK293/ABCG2 were cultured as previously described. Lysate preparation was performed as described previously. Cell membranes were prepared in exactly the same way as previously described (*J Biol Chem* 279, 19781-9 (2004); *J Biol Chem* 277, 44268-77 (2002); *Cell Physiol Biochem* 8, 246-60 (1998); and *Cancer Res* 66, 3248-55 (2006)), and final membranes were resuspended in STBS (250 mM sucrose, 150 mM NaCl, 10 mM Tris/HCl, pH7.5).

Western blot, immunoprecipitation, and flow cytometry. Western blot, immunoprecipitation, and flow cytometry analysis of drug accumulation were performed exactly as we previously described (*J Biol Chem* 279, 19781-9 (2004); *Cancer Res* 67, 4373-81 (2007)).

To determine the mechanism of ABCG2 degradation, HEK293/ABCG2 cells were first treated with 10 nM Bafilomycin $A_1$ or 2 µM MG132 for 24 hrs followed by additional treatment with 3 µM PZ39 for various times. Cell lysates were then collected for western blot analysis of ABCG2. To determine the half-life of ABCG2, HEK293/ABCG2 cells in culture were treated with 10 µg/ml cycloheximide, 3 µM PZ39, or both for various times followed by collection of cell lysates for western blot analysis of ABCG2 expression. To determine the change in antibody 5D3 staining following treatment with inhibitors, HEK293/ABCG2 cells were incubated with 10 µM PZ39, C6, C8, E2, or FTC at 37° C. for 30min before biotin-conjugated 5D3 antibody (1:100 dilution) was added and incubated for 2 hrs. Then, the cells were washed 3 times and incubated with Phycoerythrin-Streptavidin for 30 min followed by washing for 3 times and analysis by flow cytometry.

Real time RT-PCR and Cytotoxicity assay. RNA extraction and real-time RT-PCR were performed as we described previously (*Cancer Res* 66, 3248-55 (2006)). The sequences of ABCG2 primers are 5'-GGCTTTCTACCTGCAC-GAAAACCAGTTGAG-3' (forward) SEQ. ID. No. 1 and 5'-ATGGCGTTGAGACCAG-3' (reverse) SEQ. ID. No 2. The sequences of GAPDH primers are 5'-AAGGACTCAT-GACCACAGTCCAT-3' (forward) SEQ. ID. No 3, and 5'-CCATCACGCCACAGTTTCC-3' (reverse) SEQ. ID. No 4. The relative ABCG2 RNA level ($2^{\Delta CT}$) treated with inhibitors was expressed as percentage of the control (in the presence of 0.1% DMSO) where ΔCT (threshold cycle)= ($CT_{ABCG2}$–$CT_{GAPDH}$).

Cytotoxicity was determined using sulforhodamine B (SRB) colorimetric assay as previously described (*Cancer Res* 66, 3248-55 (2006)). The effect of compound inhibitors on drug resistance was determined by exposing cells to a range of concentrations of anticancer drugs such as mitoxantrone in the absence or presence of different concentrations of the inhibitor. The potency and sensitization index of the inhibitors were calculated as follows:

Potency index=$IC_{50}$(inhibitor)/$IC_{50}$(inhibitor+drug)

Sensitization index=$IC_{50}$(drug+inhibitor)/$IC_{50}$(drug)

Drug transport kinetic analysis. Drug-uptake assay using membrane vesicles was performed as we previously described (*J Biol Chem* 277, 44268-77 (2002)), using [$^3$H] mitoxantrone as ABCG2 substrate. Kinetic analysis was performed using data generated in the presence of different concentrations of [$^3$H] mitoxantrone, ATP, and PZ-39 to generate Lineweaver-Burk plot. Kinetic constants $K_m$, $V_{max}$, and $K_i$ were calculated using procedures as previously described, see, for example, *Cancer Res* 65, 1541-6 (2005) and references therein.

EXAMPLES

Figure 2:
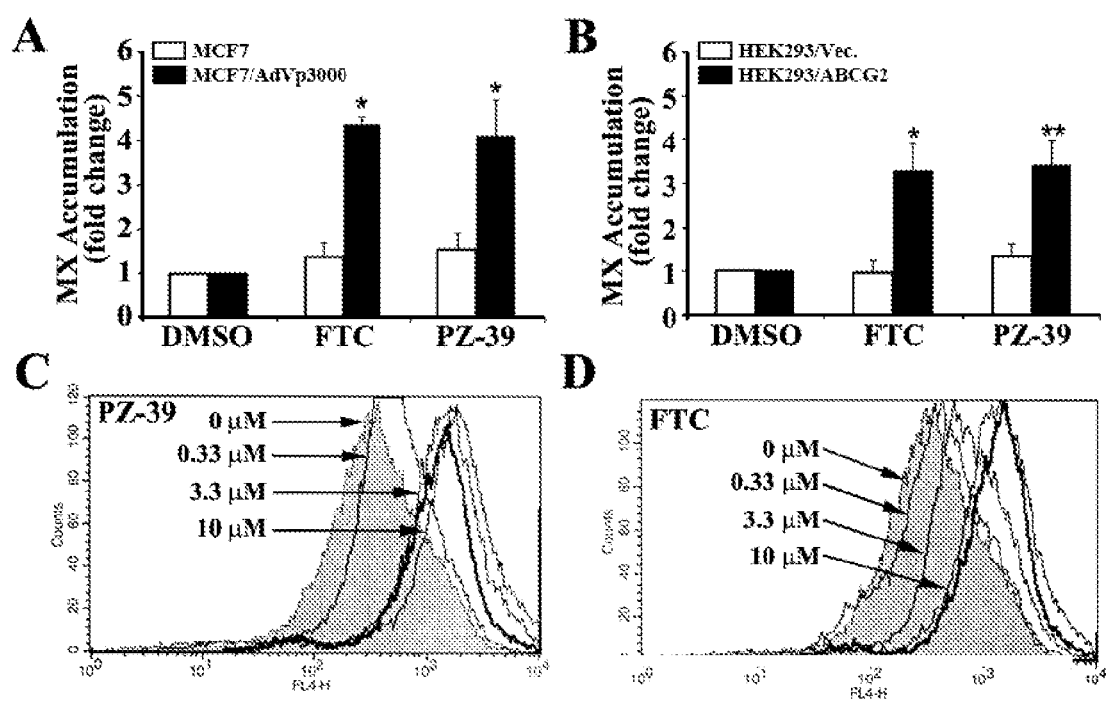
FIG. 2A. Bar graph illustrating the effect of DMSO (control), PZ-39 or FTC on the intracellular accumulation of mitoxantrone in MCF7 (open) cells or its drug-resistant subline MCF7/AdVp3000 (blackened).
FIG. 2B. Bar graph illustrating the effect of DMSO (control), PZ-39 or FTC on the intracellular accumulation of mitoxantrone in HEK 293vac cells (open) or HEK293 cells transfected with vector or ABCG2 (blackened).
FIG. 2C. Graphs showing the levels of labelled mitoxantrone accumulated in ABCG2-transfected HEK293 cells treated with various levels of PZ-39.
FIG. 2D. Graphs showing the levels of labelled mitoxantrone accumulated in ABCG2-transfected HEK293 cells treated with various levels of FTC.

Effect of compound PZ-39 on mitoxantrone accumulation. Using a rational screening of representatives of different classes of a small molecule compound library from Specs for potential inhibitors of ABCG2-mediated drug efflux, the inventors identified a compound, N-(4-chlorophenyl)-2-[(6-{[4,6-di(4-morpholinyl)-1,3,5-triazin-2-yl]amino}-1,3-benzothiazol-2-yl)sulfanyl]acetamide) with benzothiazole linked to triazine ring backbone, (named PZ-39 thereafter, see FIG. 1) that drastically reversed mitoxantrone accumulation in MCF7/AdVp3000 cells that over-express ABCG2. As shown in FIG. 2A, PZ-39 enhanced mitoxantrone accumulation in MCF7/AdVp3000 but not the parental sensitive MCF7 cells that do not produce ABCG2, suggesting that ABCG2-mediated drug efflux had been inhibited. Because MCF7/AdVp3000 cells also over-express other ABC transporters such as ABCC3 in addition to ABCG2, PZ-39 may inhibit ABC transporters other than ABCG2, causing increased mitoxantrone accumulation. To directly test if PZ-39 inhibits ABCG2, similar studies were performed using ABCG2-transfected stable HEK293 (HEK293/ABCG2) cells. As shown in FIG. 2B, pre-incubation of cells with PZ-39 enhanced intracellular mitoxantrone accumulation in HEK293/ABCG2 but not in the vector-only-transfected control cells. Thus, PZ-39 likely inhibits ABCG2-mediated mitoxantrone efflux. FIGS. 2A and 2B also show that PZ-39 at 3.3 µM achieved an equivalent level of effect to the known specific ABCG2 inhibitor FTC at 10 µM, suggesting that PZ-39 may be ~3 times more potent than FTC. These data are means±SD from three independent experiments (*P<0.05; **P<0.01 compared with DMSO vehicle).

To further investigate the potency of PZ-39 for ABCG2, the dose response effect of PZ-39 on mitoxantrone accumulation in HEK293/ABCG2 cells were determined using flow cytometry. As illustrated in FIG. 2C, the intracellular mitoxantrone level was increased by PZ-39 in a dose-dependent manner. At 3.3 µM, PZ-39 completely restored intracellular mitoxantrone level in HEK293/ABCG2 cells to level found in control cells. Referring now to FIG. 2D, FTC, on the other hand, achieved similar level of effect only at the 10 µM level, supporting the argument that PZ-39 is more potent inhibitor of ABCG2 than is FTC.

Figure 3:
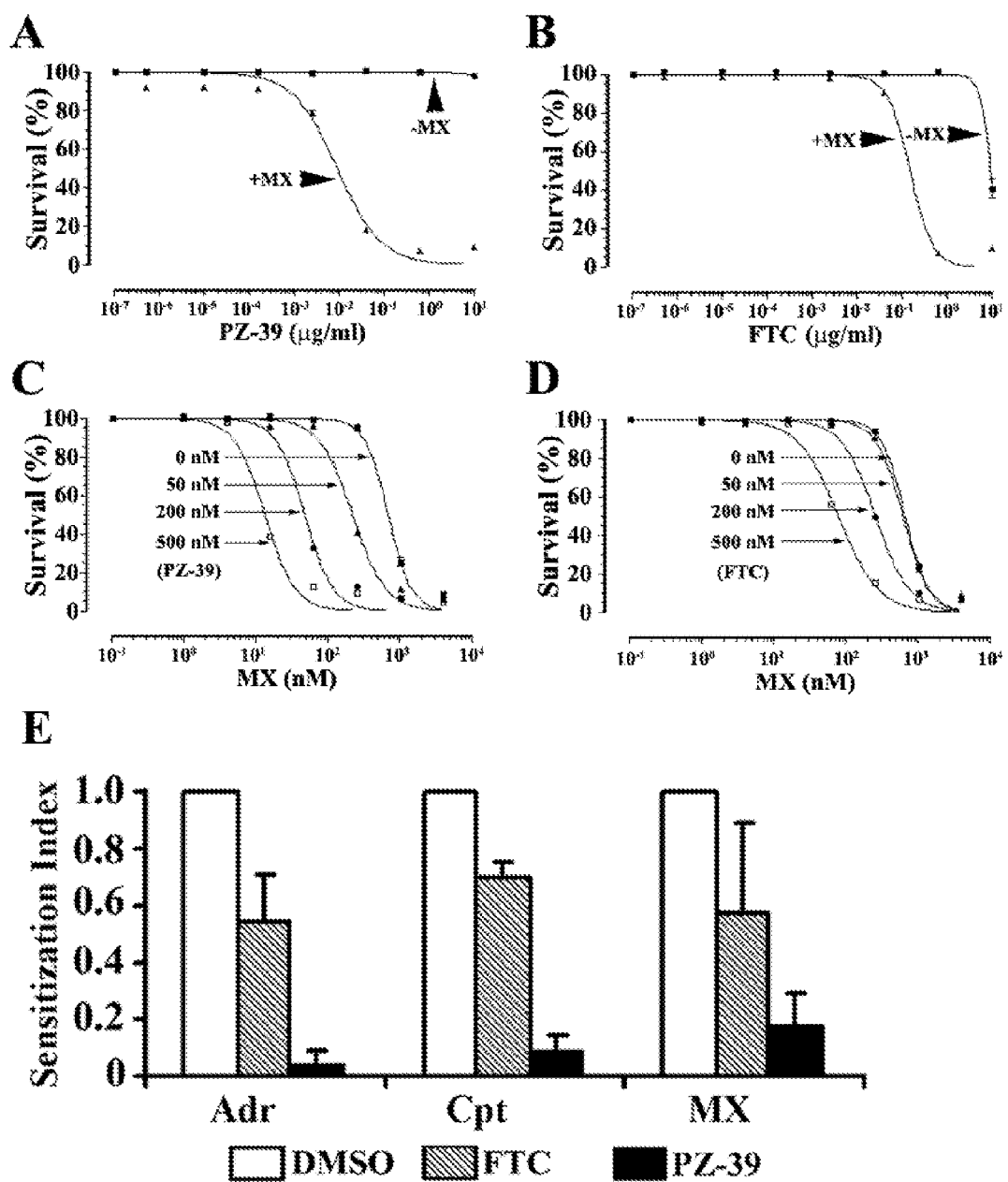
FIG. 3A. Graph of the survival percentage of HEK293/ABCG2 cells versus µg ml-1 of PZ-39. Cells were treated either with (+) or without (−) 0.1 µM (IC$_{10}$) mitoxantrone.
FIG. 3B. Graph of survival percentage of HEK293/ABCG2 cells versus µg ml-1 of FTC. Cells were treated either with (+) or without (−) 0.1 µM (IC$_{10}$) mitoxantrone.
FIG. 3C. Graph of survival percentage of HEK293/ABCG2 cells versus nM of mitoxantrone measured in the absence of and presence of 50, 200 and 500 nm of PZ-39.
FIG. 3D. Graph of survival percentage of HEK293/ABCG2 cells versus nM of mitoxantrone measured in the absence of and presence of 50, 200 and 500 nm of FTC. The data in FIGS. 3A, 3B, 3C and 3D are representative of four independent experiments FIG. 3E. Bar graph of the sensitization index of drug-selected MCF7/AdVp3000 cells treated with DMSO (white), 200 nM FTC (gray) or 200 nM PZ-39 (black) measured in the presence of adriamycin, camptothecin, or mitoxantrone in the DMSO (vehicle).

Sensitization of drug resistance by PZ-39. To investigate the potential use of PZ-39 as a chemo-sensitizer of ABCG2-mediated drug resistance, the effect of PZ-39 on drug response of HEK293/ABCG2 cells was determined in the absence or presence of 0.1 µM mitoxantrone which by itself produced ~10% cell killing. Referring now to FIGS. 3A and 3B, it appears as though that PZ-39 is not as cytotoxic to HEK293/ABCG2 cells; it has an $IC_{50}$ that is not measurable within the concentration range used, whereas the $IC_{50}$ value for FTC is on the order of ~25 µM. The $IC_{50}$ values of PZ-39 and FTC required to sensitize mitoxantrone resistance is ~13 nM and ~326 nM, respectively.

Accordingly, the potency index of PZ-39 is estimated to be about >1923 whereas the potency index of FTC is estimated to be ~76 (Table 1).

TABLE 1

Potency index of PZ-39 in sensitizing drug resistance of HEK293/ABCG2 cells

| Inhibitors | $IC_{50}$ (µM) | | Potency Index[b] |
|---|---|---|---|
| | Inhibitor alone | Inhibitor + MX[a] | |
| PZ-39 | >25[c] | 0.013 ± 0.001 | >1923 |
| FTC | 25 ± 1.4 | 0.326 ± 0.086 | 76 |

[a]MX = 100 nM mitoxantrone which produces ~10% inhibition of growth ($IC_{10}$).
[b]Potency Index = ratio of inhibitor $IC_{50}$ in the absence and presence of anticancer drug mitoxantrone at low concentration (<$IC_{10}$).
[c]PZ-39 has no measurable cytotoxicity within the concentration range used and its $IC_{50}$ value was estimated to be bigger than that of FTC which is ~25 µM.

Referring now to FIG. 3C, To further investigate the inhibitory activity of PZ-39 on ABCG2, the effects of PZ-39 on mitoxantrone cytotoxicity in HEK293/ABCG2 cells was evaluated in the presence of three different concentrations of PZ-39 (50, 200, or 500 nM) or 0 in the vehicle-only control (0.1% DMSO). As shown in FIG. 3C, PZ-39 at 50 nM significantly reduced the $IC_{50}$ of mitoxantrone with a sensitization index of 0.4 (Table 2). At 500 nM, the sensitization index of PZ-39 is 0.04, whereas that of FTC at the same concentration is 0.26 (see FIG. 3D and Table 2). These results demonstrate that PZ-39 is a very potent inhibitor of ABCG2.

TABLE 2

Sensitization index of PZ-39 in HEK293/ABCG2 cells

| Inhibitors | Mitoxantrone $IC_{50}$ (nM) | | |
|---|---|---|---|
| | 50 nM (SI[a]) | 200 nM (SI) | 500 nM(SI) |
| DMSO | 551.1 ± 20.8 | | |
| PZ-39 | 216.7 ± 5.3 (0.39) | 53.2 ± 13.2 (0.10) | 23.2 ± 14.2 (0.04) |
| FTC | 467.8 ± 42.6 (0.85) | 254.7 ± 7.9 (0.46) | 143.1 ± 39.3 (0.26) |

[a]SI = sensitization index, determined by dividing $IC_{50}$ of mitoxantrone in the presence of inhibitors by $IC_{50}$ of mitoxantrone in the presence of DMSO vehicle.

To investigate if PZ-39 can reverse ABCG2-mediated multidrug resistance in a drug resistant cancer cell line, drug-selected MCF7/AdVp3000 cells were used and tested two additional anticancer drug substrates of ABCG2, Adriamycin and Camptothecin ((S)-4-ethyl-4-hydroxy-1H-pyrano[3',4':6,7]indolizino[1,2-b]quinoline-3,14-(4H,12H)-dione) were tested. As illustrated in FIG. 3E, PZ-39 at 200 nM drastically reduced the resistance of MCF7/AdVp3000 to adriamycin and camptothecin, similar to the results obtained with mitoxantrone. By contrast, the control, which used FTC, exhibited a much lower sensitization effect for all three drugs when compared to PZ-39 used at the same concentration. Data was collected using the SRB assay. The sensitization index was calculated using the $IC_{50}$ of mitoxantrone in the absence or presence of PZ-39 and FTC, respectfully. The data shown are mean±SD of three independent experiments.

Figure 4:
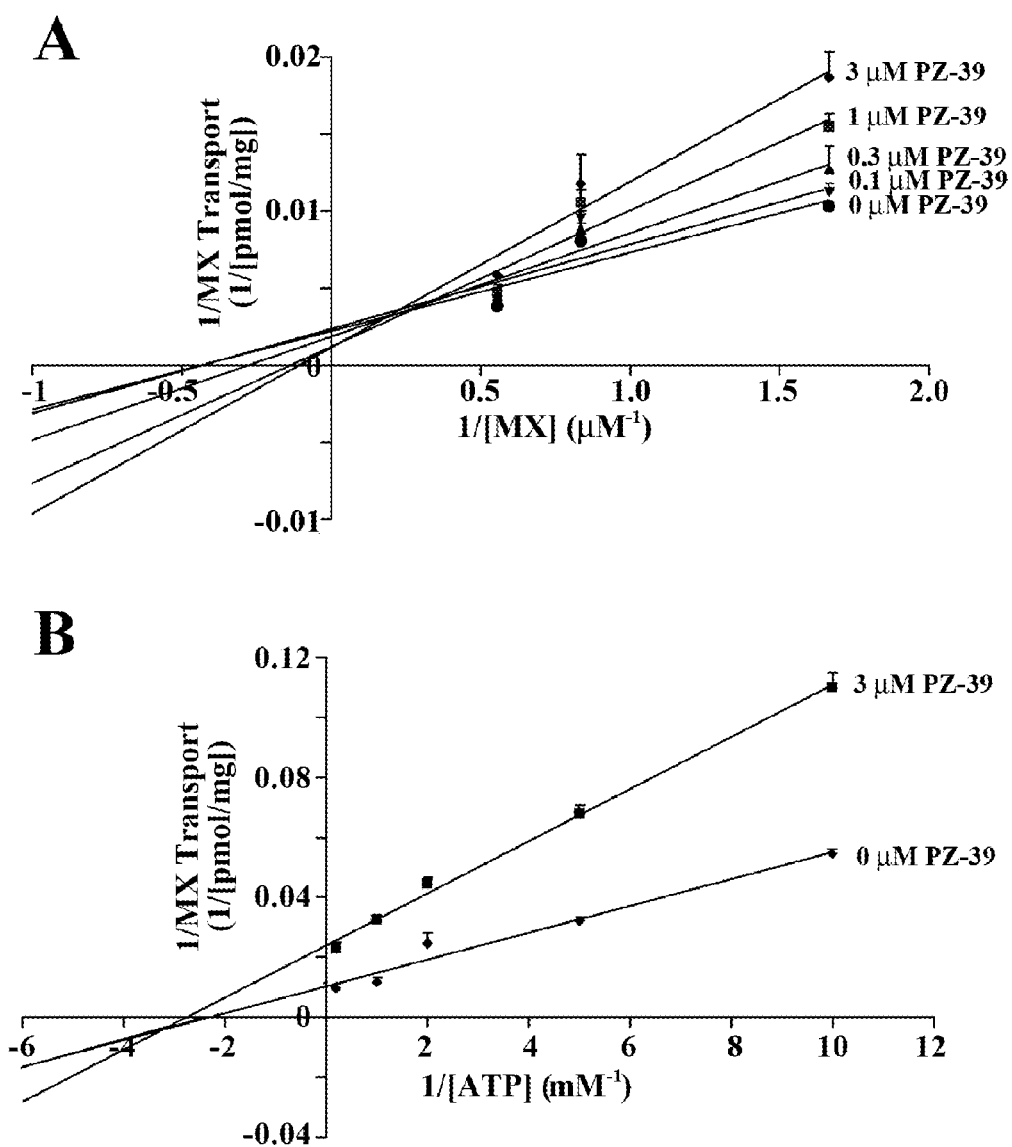
FIG. 4A. Lineweaver-Burk plot elicited the effect of different amounts of PZ-39 inhibition on ABCG2-mediated mitoxantrone uptake on inside-out vesicles made from HEK293/ABCG2 cells as a function of A7P concentrations.
FIG. 4B. Lineweaver-Burk plot illustrating the effect of either 0 or 3 μM PZ-39 on ABCG2-mediated mitoxantrone uptake measured at different concentrations of ATP.

The compound PZ-39 appears to have 2 modes of action. Referring now to FIG. 4, in order to study the mechanism of PZ-39 action in inhibiting ABCG2-mediated drug transport, the kinetics of PZ-39 inhibition was first investigated using isolated inside-out membrane vesicles (from HEK293/ABCG2). The change in mitoxantrone uptake in the presence of different concentrations of PZ-39 was determined. Inside-out plasma membrane vesicles cells were incubated with 0.6, 1.2, and 1.8 µM [$^3$H]mitoxantrone (A) or with 0.1, 0.2, 0.5, 1, and 5 mM ATP together with 0.6 µM [$^3$H] mitoxantrone. As shown in the Lineweaver-Burk plot (FIG. 4A), the data were collected by exposing the vesicles to 3 µM of PZ-39 at 37° C. for 5 min followed by determination of mitoxantrone uptake. The $K_m$ and $V_{max}$ of mitoxantrone transport in the absence of PZ-39 were estimated to be 2.3 µM and 455 pmol/mg protein, respectively. It appears that both the $K_m$ and $V_{max}$ of mitoxantrone transport have been decreased in the presence of PZ-39 with an estimated $K_i$ of ~0.52 µM, suggesting a mixed type of inhibition. Because mitoxantrone transport and ATP hydrolysis by ABCG2 is coupled to ATP uptake, we performed another experiment using ATP as the varied substrate. Referring now to FIG. 4B, both the $K_m$ and $V_{max}$ of mitoxantrone transport were also altered by PZ-39. Thus, the coupling process of mitoxantrone transport and ATP hydrolysis may be inhibited by PZ-39 via mixed type of inhibition. Likely, PZ-39 binds to a different site on ABCG2 from both mitoxantrone and ATP. The data shown are mean±S.D. of three independent experiments.

Figure 5:
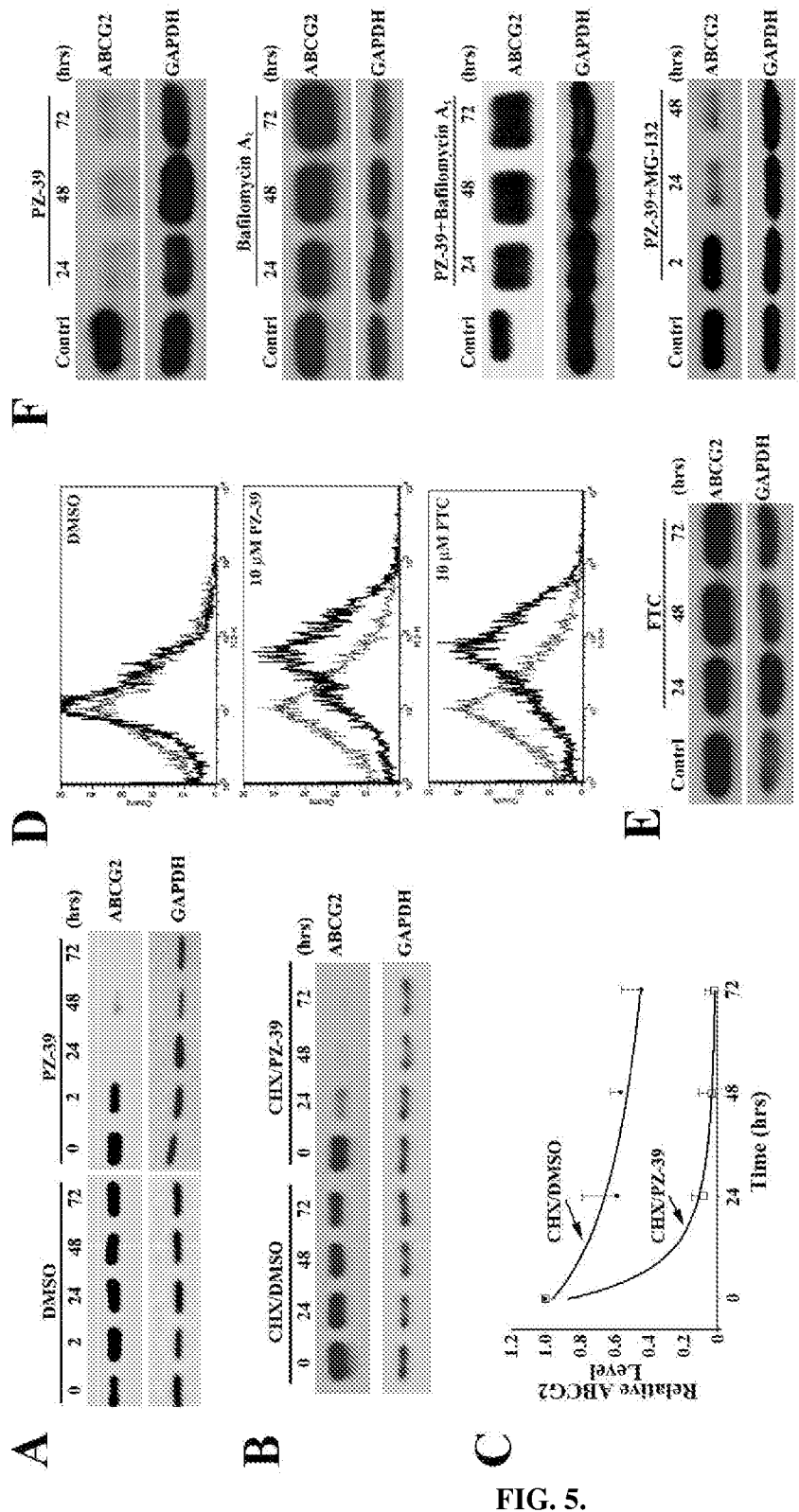
FIG. 5A. Western Blot analysis illustrating the effect of exposing HEK293/ABCG2 cells to either a control (DMSO carrier) or 3.3 μM PZ-39 on the steady state levels of either ABCG2 (upper row) or GAPDH (lower row).
FIG. 5B. Western Blot analysis illustrating the effect of exposing HEK293/ABCG2 cells to either a control (DMSO) or 3.3 μM PZ-39 on the steady state levels of ABCG2 (upper row); before exposure to PZ-39 the cells were treated with cycloheximide (CHX) (5 μg/ml).
FIG. 5C. Graph of the relative levels of ABCG2 measured over time after treatment with either CHX/DMSO (control) or CHX/PZ-39. The data shown are mean+S.D of four experiments that measured ABCG2 levels by western blot analysis using Scion Imaging.
FIG. 5D. Graphs illustrating the effects of different compounds on the conformation of ABCG2 expressed HEK293/ABCG2 cells treated without (thin line) or with (thick line) DMSO vehicle (top panel), 10 μM PZ-39 (middle panel) or 10 μM FTC (lower panel).
FIG. 5E. Western blots illustrating the effect of 10 μM FTC on ABCG2 expression (upper row) in HEK293/ABCG2 cells treated with FTC for control, 24, 48 or 72 hours, the lower row illustrates the level of GAPDH in the samples.
FIG. 5F. Western blots illustrating the effects of: 3 μM PZ-39 (top panel); 10 nM bafilomycin $A_1$ (second panel form top); both PZ-39 and bafilomycin $A_1$ (third panel form top); and 3 μM PZ-39 plus 2 μM MG-132 (bottom panel) on ABCG2 levels (top row in each panel) measured in HEK293/ABCG2 cells.

Referring now to FIG. 5, in order to further examine the mechanism of PZ-39's effect on ABCG2, we performed a western blot analysis of ABCG2 expression levels in HEK293/ABCG2 cells following treatment with PZ-39. As illustrated in FIG. 5A, the steady state level of ABCG2 protein drastically decreased at 1 day after PZ-39 treatment with a marginal decrease at 2 hrs. This finding suggests that PZ-39 may have two modes of action; inhibition of ABCG2 activity (acute effect) and reduced levels of ABCG2 (chronic effect). These results are ABCG2 and consistent with our observation that PZ-39 is about 3 times better than FTC in drug accumulation assay (acute effect) but ~7 times more potent in drug sensitization assay (chronic effect).

Figure 8:
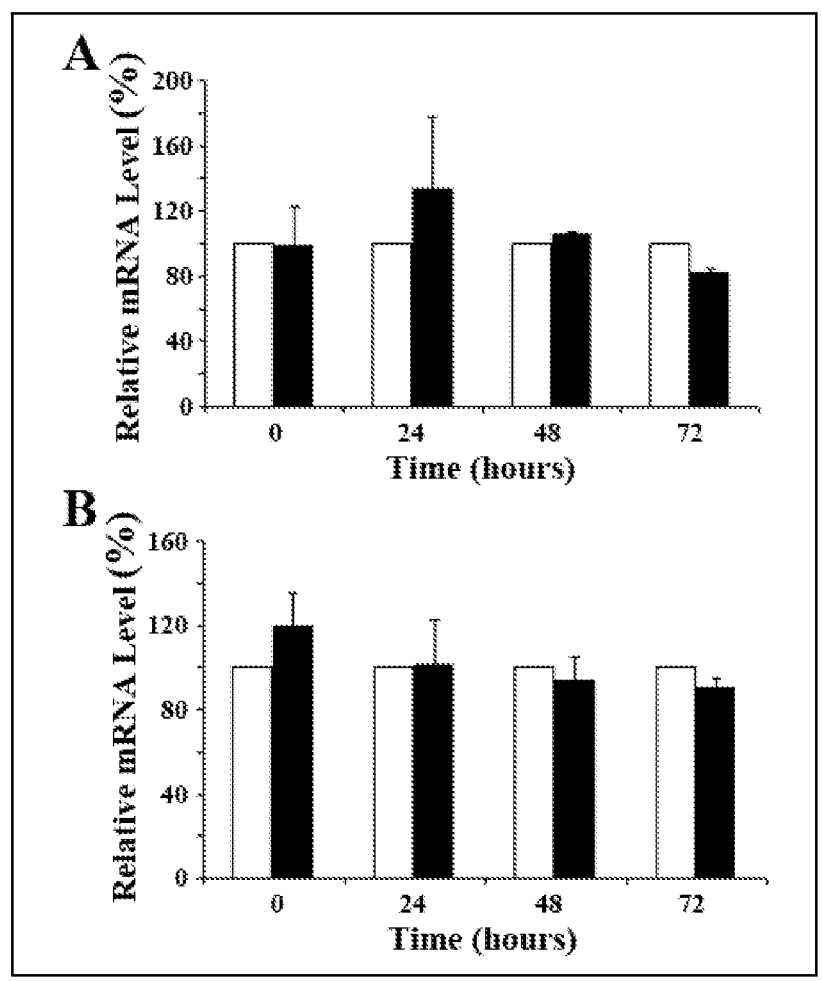
FIG. 8. Bar graph illustrating the effect of DMSO vehicle (open bar) or PZ-39 (filled bar) on ABCG2 mRNA levels in MCF7/AdVp3000 cells (panel A) or HEK293/ABCG2 cells (panel B).

Referring now to FIG. 8, in order to determine if the chronic effect of PZ-39 on ABCG2 expression is at the mRNA level, we performed real-time RT-PCR analysis was performed of MCF7/AdVp3000 and HEK293/ABCG2 cells treated with PZ-39 for various times up to 3 days. No significant changes in ABCG2 mRNA levels were found following PZ-39 treatment in either cell line. Thus, it is unlikely that PZ-39 affects ABCG2 expression at its mRNA level. Next, the possibility that the binding of PZ-39 to ABCG2 may target it to degradation was examined. To test this possibility, HEK293/ABCG2 cells were pre-treated with cycloheximide followed by treatment with PZ-39 at various times to determine ABCG2's degradation rate. As illustrated in FIG. 5B, the loss of ABCG2 in cells treated with a combination of PZ-39 and cycloheximide was much faster than that of the control treatment without PZ-39. Referring now to FIG. 5C, the half-life of ABCG2 in the presence of PZ-39 is estimated to be ~5 hrs whereas it is stable with an estimated half-life of ~54 hrs in the control. Thus, PZ-39 likely accelerates degradation of ABCG2 protein.

PZ-39 induces conformational change of ABCG2 and its degradation in lysosomes. The accelerated degradation of ABCG2 by PZ-39 may be due to the binding of PZ-39 to ABCG2 which induces conformational changes that target ABCG2 for degradation. To determine if binding of PZ-39 potentially causes conformational changes of ABCG2, the monoclonal antibody 5D3 was used. It has been reported that 5D3 binds to the surface of ABCG2 more readily in the presence of ABCG2 inhibitors, presumably due to inhibitor-induced conformational changes.[7,10]

Referring now to FIG. 5D The conformation of the ABCG2 was followed by staining the proteins with the fluorescent labelled monoclonal antibody 5D3 and flow cytometry analysis. A shift to the right is indicative of a change in the conformation of ABCG2 that in turn effects the binding of 5D3. Treatment with the vehicle (DMSO) had no effect (top panel) while treatment with either FTC or PZ-39 had comparable effects on the structure of ABCG2. As shown in FIG. 5D, PZ-39 caused an increase in 5D3 staining, suggesting a possible conformational change of ABCG2 upon PZ-39 binding. FTC, a compound known to alter the conformation of ABCG2, also increased 5D3 staining as expected. However, it did not affect the level of ABCG2 (FIG. 5E), suggesting that the conformational change induced by FTC and PZ-39 may be different. These results are consistent with other data, including western blotting studies, demonstrating that only treatment with PZ-39 and not FTC has the effect of reducing the level of ABCG2 in the cells.

Referring now to FIG. 5F, to further determine the mechanism of PZ-39-induced ABCG2 degradation, we employed bafilomycin $A_1$, an inhibitor of protein degradation in lysosomes, and MG-132, a proteosome inhibitor. Cells were treated with 3 μM PZ-39 (top panel), 10 nM Bafilomycin $A_1$ (panel second from top) co-treatment of cells with 10 nM bafilomycin $A_1$ and 3 μM PZ-39 inhibited PZ-39-induced ABCG2 degradation (third panel from top) whereas co-treatment with 2 μM MG-132 and bafilomycin $A_1$ PZ-39 did not (bottom panel), indicating that PZ-39-induced ABCG2 degradation is likely lysosome-dependent. Samples were taken at times before exposure of cells (control) and 24, 48 and 72 hours after exposure in the top 3 panels, and before, 2, 24 and 48 hours after exposure (bottom panel). Taken together, it can be concluded that the binding of PZ-39 causes a conformational change in ABCG2 that targets it for lysosomal for degradation.

Structure activity relationship analysis of PZ-39 analogues. To investigate the functional groups of PZ-39, a structure-activity relationship (SAR) analysis of PZ-39 was performed using various compounds that include the core structure of PZ-39 functionalized as illustrated using the nomenclature in the table presenting in FIG. 6A. A total of 29 derivatives of PZ-39 each with one or more alterations were obtained. The $R_1$ groups at 4' and 6' positions are the same in PZ-39 and all derivatives with $R_1$ substitutions in the triazine ring also have $R_2$ modifications. These derivatives together with PZ-39 (designated as D5 in FIG. 6A) were tested for their ability to inhibit ABCG2-mediated decrease in mitoxantrone accumulation. Representations of functional groups are also shown with indication of favorable (thick arrows) or unfavorable substitutions (thin-crossed arrows); the structure of Fumitremorgin C (FTC) is also shown. The table includes designations for the compounds as well as their fluorescence intensity ability to inhibit the efflux of MX from the cells, reported in the table as Fluorescence Intensity, which is proportional to the amount of the fluorescent compound MX sequestered by the cells.

Figure 6B:
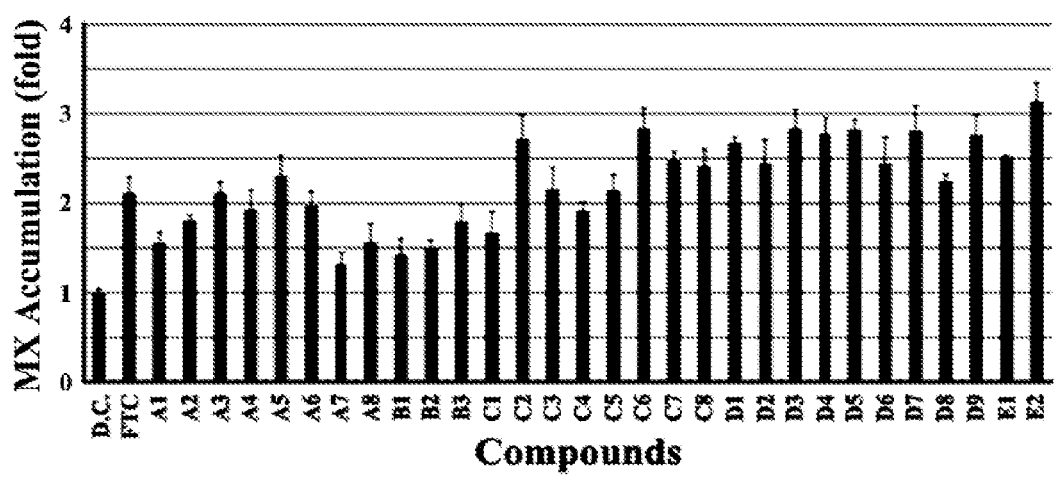
FIG. 6B. Bar graph illustrating the fold accumulation of mitroxantrone (MX) in HEK293/ABCG2 cells measured as a function of the presence of 3 μM of various PZ-39 derivatives as well as FTC and DMSO vehicle (D.C.). Data shown are mean±S.D of triplicate experiments. This figure uses the nomenclature of FIG. 6A, e.g., D5=PZ-39.

Referring now to FIG. 6B, a graph illustrating the normalized amount of MX sequestered by the cells in the presence of the same amounts of different compounds (compounds with different substitutions of $R_1$ and $R_2$ groups) exhibited either decreased or increased inhibitory activities as compared to PZ-39 in a drug transport assay. Sixteen of these derivatives are better than FTC and three of them exhibit similar or an increased inhibitory activity as compared to PZ-39 (D5). FIG. 6A also summarizes the substitutions with positive and negative impact on PZ-39 activity. Briefly, substitution at $R_2$ with N-t-butyl acetamide (C6) and N-phenylacetamide (D9) did not have much effect on the molecule's inhibitory activity. Whereas, acetate ($C_1$) and N-furanacetamide ($C_5$) substitutions decreased the molecule's inhibitory activity. Compared with compound D9, which has an activity similar to PZ-39. Compound A2 which includes a morpholine substitution at $R_1$ exhibited decreased inhibitory activity (FIG. 6B). Similarly, a piperidine substitution at $R_1$ decreased inhibitory activity (FIG. 6B). Phenylamino substitution at $R_1$ (E2) substantially increased inhibitory activity (compare with compound $C_4$, FIG. 6B). Taken together, the order of ABCG2-inhibitory activity at R1 substitutions appears to be as follows: phenylamino>morpholine>piperidine≈pyrrolidine and the order of ABCG2-inhibitory activity at R2 substitutions is N-t-butylacetamide≈N-phenylacetamide>N-furanacetamide>acetate.

Figure 6C:
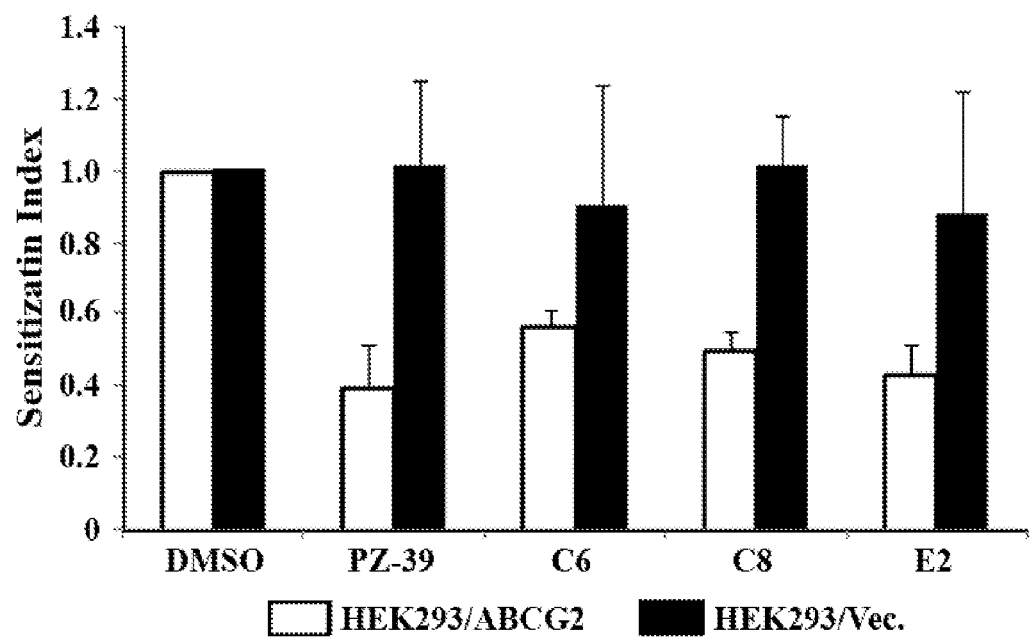
FIG. 6C. Bar graph illustrating the sensitization index of HEK293/ABCG2 cells (open) or HEK293/ABCG2 cells (closed).

Referring now to FIG. 6C, in order to further determine the effect of these derivatives on ABCG2-mediated drug resistance, SRB assays using HEK293/ABCG2 cells were performed with 3 selected analogue compounds, C6, C8, and E2 and compared them with the effect of PZ-39 on the assay. The sensitization value graphed in FIG. 6B was calculated using an SRB assay to measure the $IC_{50}$ values of mitoxantrone.

The data are mean±S.D. of four independent experiments. All three compounds tested have similar sensitization indexes to mitoxantrone as PZ-39 at the 50 nM level in HEK293/ABCG2 cells while having no effect on HEK293/Vec control cells.

Figure 6D:
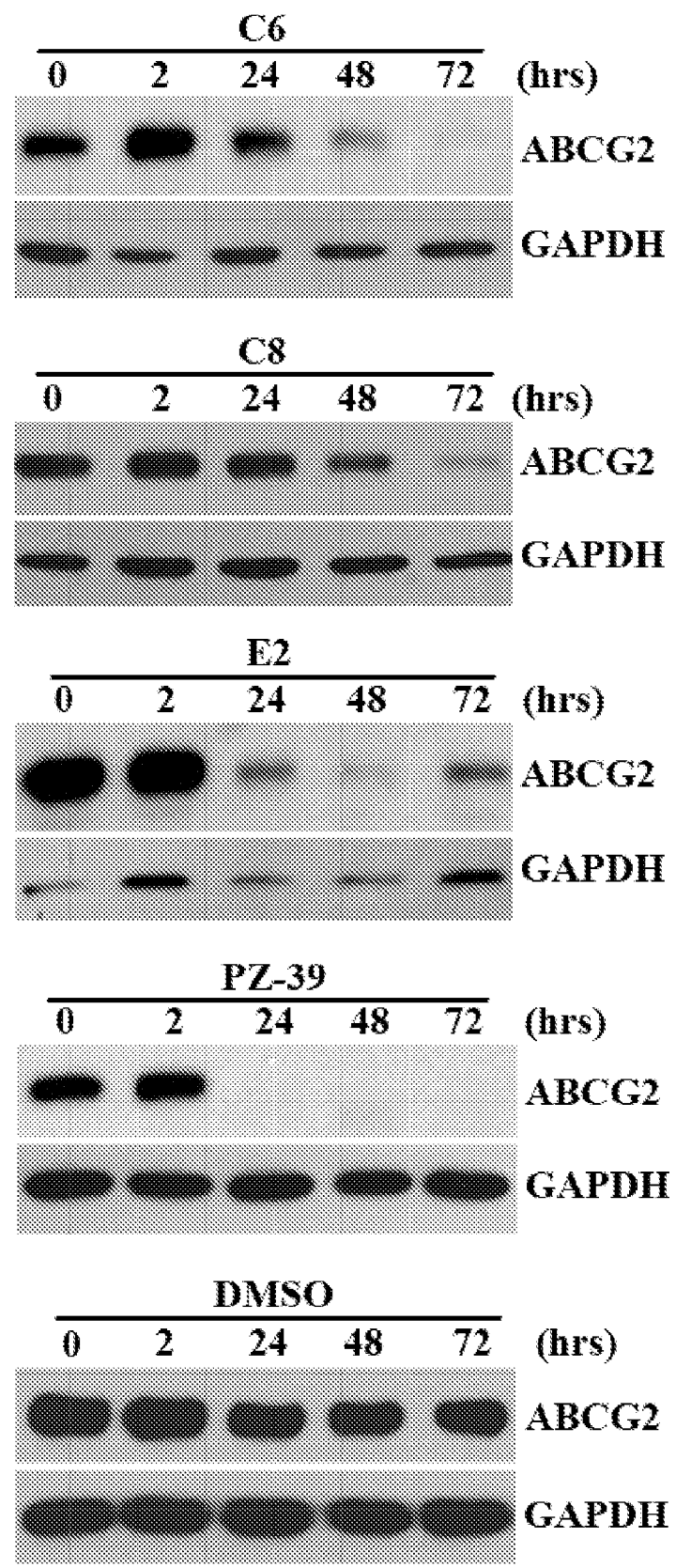
FIG. 6D. Western blot analysis illustrating the effect of 3 μM of : C6(top), 3 μM C8 (second from top), E2 (third from top), 3 μM PZ-39 (forth from top) or DMSO vehicle (bottom) on the level of ABCG2 in HEK293/ABCG2 cells.

Referring now to FIG. 6D, to measure the chronic effect of these derivatives on ABCG2 expression, we performed a western blot analysis following treatment with 3 µM of C6, C8, E2, or PZ-39, respectively, or DMSO (control) for various times up to 3 days. All 4 compounds caused in of ABCG2 levels. The top row in each panel indicates the level of ABCG2 and the bottom row in each panel indicates the level of GAPDH; samples were drawn at times 0, 2, 24, 48 and 72 hours after exposure to the indicated compound. All 3 of the 3 PZ-39 derivatives tested also caused conformational changes in ABCG2 similar to PZ-39. Thus, it appears likely that these derivatives all operate via a mechanism similar to how PZ-39 is now thought to operate.

Figure 6E:
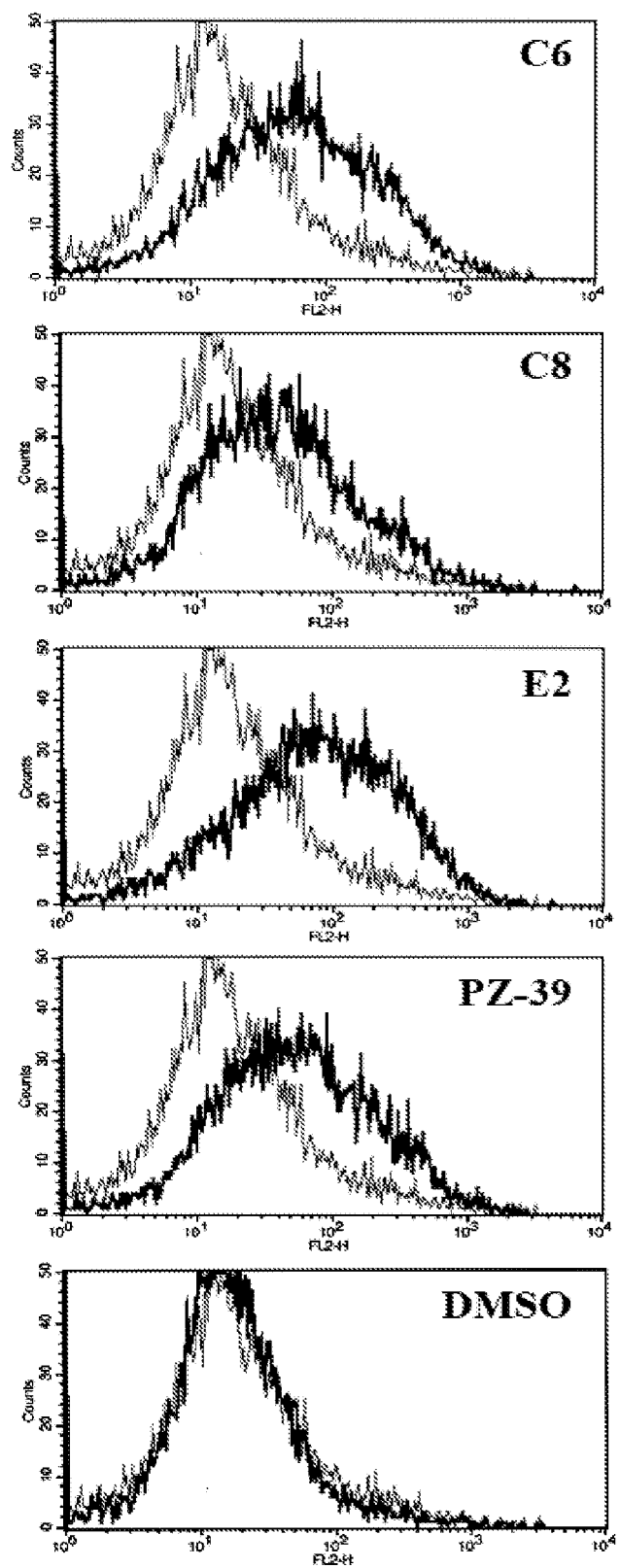
FIG. 6E. Graphs illustrating the effect of treating HEK293/ABCG2 without (thin line) or with (thick line) C6 (top panel), C8 (second panel), E2 (third panel), PZ-39 (forth panel) or DMSO (bottom panel) on the conformation of ABCG2.

Referring now to FIG. 6E, graphs illustrating the effect of 3 µM of C6, or C8, or E2, or PZ-39 or DMSO (control) the conformation of ABCG2. HEK/ABCG2 cells were treated without (thin line) or with (thick line) the compounds indicated in the panels and then stained with the monoclonal antibody 5D3 and analyzed by flow cytometry.

Figure 7:
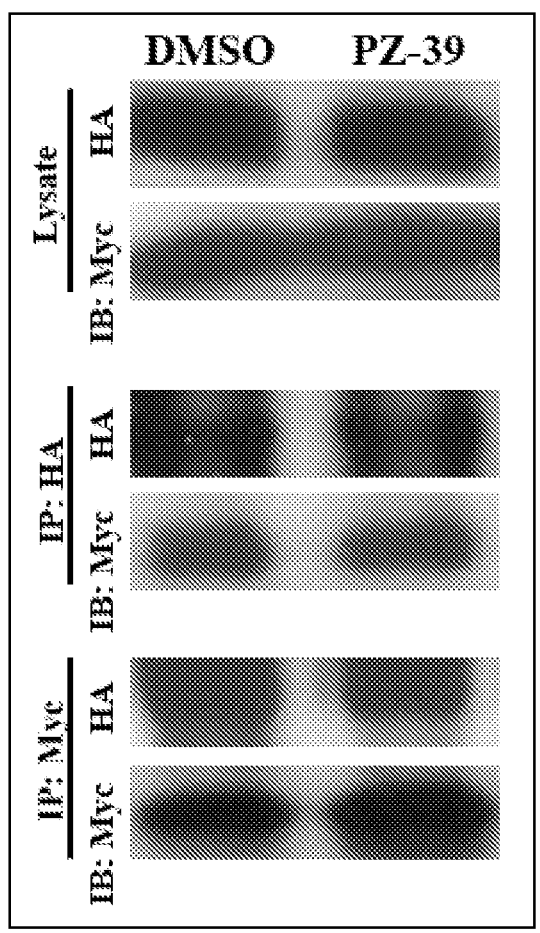
FIG. 7. Western blots illustrate the effect of PZ-39 on ABCG2 oligomerization. HEK293 cells co-transfected with Myc- and HA-tagged ABCG2 were exposed to either DMSO (right side) or 3.3 μM PZ-39 (left side) for 6 hrs; cell lysates were immunoprecipitated with anti-Myc or anti-HA monoclonal antibody followed by western blot analysis probed using anti-HA and anti-Myc antibody.

Effect of PZ-39 on the oligomerization of ABCG2. Referring now to FIG. 7, the effect of PZ-39 on the oligomerization of ABCG2 was measured since ABCG2 has been suggested to function as a homodimer or a higher form of oligomers. For this purpose, co-immunoprecipitation of two differentially tagged ABCG2 was performed as previously described (*Cancer Res* 67, 4373-81 (2007)) following a 6-hr treatment with PZ-39 at 3.3 µM. However, no effect of PZ-39 on ABCG2 co-immunoprecipitation was found, these results suggest that PZ-39 does not effect oligomerization the of ABCG2.

Figure 9:
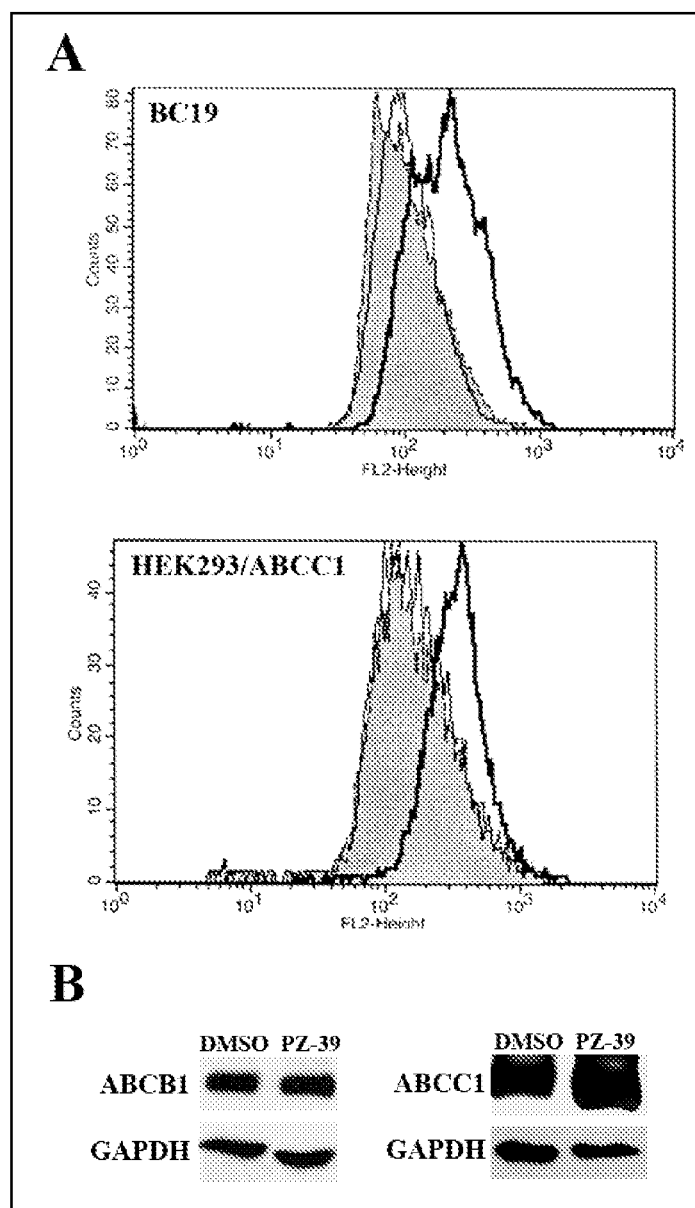
FIG. 9A. Graph illustrating the effect of treating cells with 3 μM PZ-39 for 30 minutes on the intercellular accumulation of adriamycin in MCF7 cells transfected with BC19 which over-express ABCB1 (upper panel) or HEK293/ABCC1 cells which over-express ABCC1 (lower panel).
FIG. 9B. Western blots illustrating the expression of ABCB1 (right side, upper band) or GAPDH (lower band) or ABCC1 (left side, upper band) or GAPDH (lower band).
Figure 10:
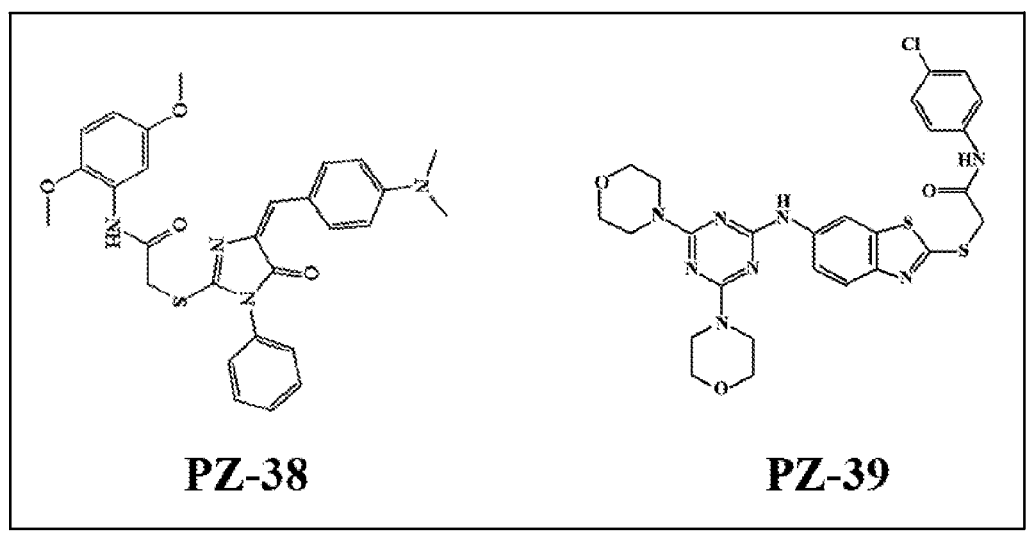
FIG. 10. Comparison of the chemical structures of PZ-38 and PZ-39.

Effect of PZ-39 on ABCB1- or ABCC1-mediated drug transport. Referring now to FIG. 9 A, in order to investigate the specificity of PZ-39, the effect of 3 µM PZ-39 on ABCB1 and ABCC1-mediated decrease in intracellular adriamycin accumulation was tested using MCF7 cells transfected with a vector enabling them to over-express ABCB1 (BC19) and HEK293/ABCC1 cells which over-express ABCC1. Cells were treated with DMSO vehicle or 3.3 µM PZ-39 for 30 min followed by determination of intracellular accumulation of Adriamycin (A) or treated with DMSO vehicle or 3.3 µM PZ-39 for 3 days. Thick lines represent control MCF7 cells transfected with vector for BC19 or HEK293 cells transfected with vector for HEK293/ABCC1. The gray areas and thick lines represent values collected using cells treated with DMSO and PZ-39, respectively. It was found that PZ-39 had no effect on the activity of either ABCB1 or ABCC1 in decreasing adriamycin accumulation (FIG. 9A).

Referring now to FIG. 9B, western blots demonstrated that PZ-39 had no effect on the steady state levels of either ABCB1 or ABCC1. GAPDH was used as a protein loading control in these assays. Cells were assayed for these proteins after 3 days of treatment with PZ-39. These results are consistent with PZ-39 being either specific, or at least highly selective, for ABCG2.

Concentration-dependent effect of PZ-38 on mitoxantrone accumulation. To further investigate the relative inhibitory potency of PZ-38 for ABCG2, the concentration-dependent effect of PZ-38 on accumulation in both MCF7/AdVp3000 cells (upper panel) and HEK293/ABCG2 cells (lower panel) was measured by flow cytometry. Referring now to FIG. 9, the intracellular mitoxantrone level in both ABCG2-overexpressing cell lines was increased by the addition of PZ-38 in a dose-dependent manner. The accumulation of mitoxantrone decreased markedly in the absence of PZ-38 in both ABCG2-overexpressing cells (shadow peak), as compared with that in ABCG2-negative cells (bold line). However, at a concentration of 10 µM, PZ-38 was not able to completely restore mitoxantrone accumulation, suggesting that it is less effective in this capacity than either PZ-39 or FTC.

Reversal of Drug Resistance by PZ-38. Referring now to FIG. 11A, in order to determine if PZ-38 could sensitize cells that over-express ABCG2 to anticancer drugs, we tested the effect of DMSO, 3.0 mM FTC or 3.8 mM PZ-38 on MX accumulation in ABCG2-transfected HEK293 (solid) or HEK293/Vec. control cells (open). Referring now to FIG. 11B, in order to determine if PZ-38 could sensitize cells that over-express ABCG2 to anticancer drugs, we tested the effect of DMSO, 3.0 mM FTC or 3.8 mM PZ-38 on MX accumulation in ABCG2-transfected MCF7/AdVp3000 (solid) or MCF7 control cells (open).

Figure 12:
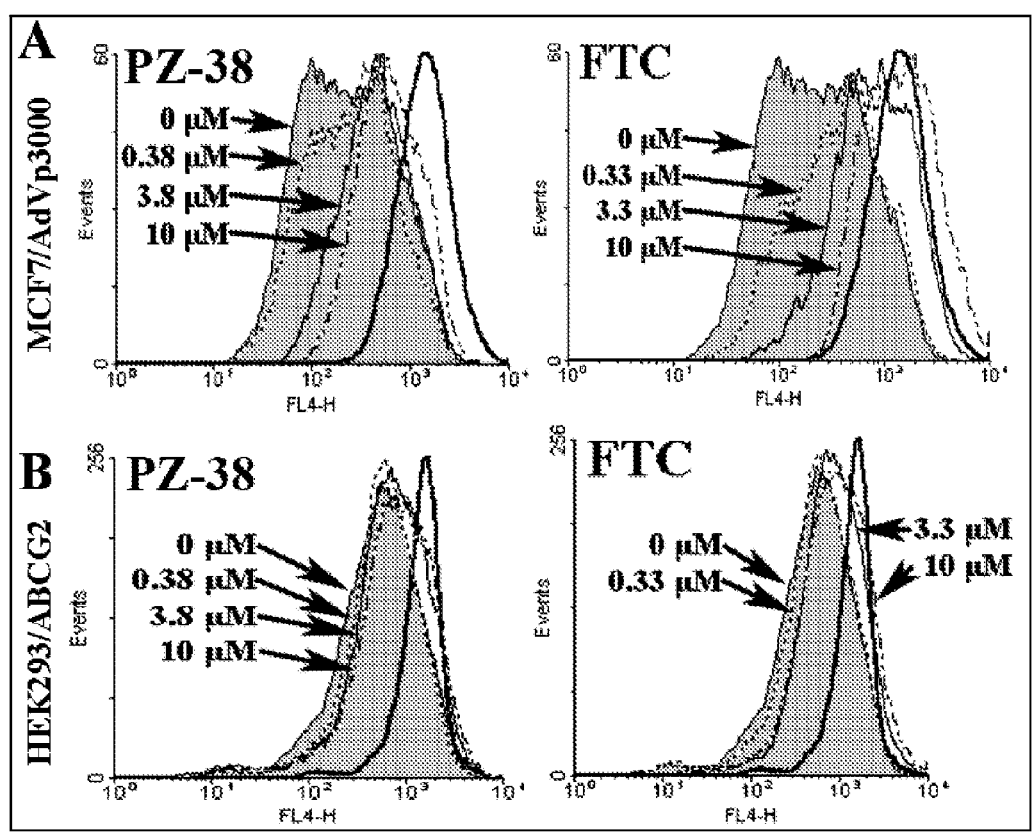
FIG. 12A. Graph illustrating the concentration-dependent effect of PZ-38 (left panel) or FTC (right panel) of mitoxantrone accumulation in MCF7/AdVp3000 cells in the presence (thin line) or absence (shadow) of different concentrations of PZ-38 in the and HEK293/ABCG2. The solid line indicates the accumulation of mitoxantrone in control cells, MCF7 cells.
FIG. 12B. Graph illustrating the concentration-dependent effect of PZ-38 (left panel) or FTC (right panel) on mitoxantrone accumulation in HEK293/ABCG2 cells in the presence (thin line) or absence (shadow) of different concentrations of PZ-38. The solid line indicates the accumulation of mitoxantrone in control cells, HEK293 cells.

The activity of ABCG2 was measured in the presence of 3 different concentrations of PZ-38 (50, 200, 500 nM) and in the presence of only the vehicle (0.1% DMSO). As illustrated in FIG. 12B, PZ-38 effected ABCG2-mediated drug resistance is in dose-dependent manner.

Figure 13A:
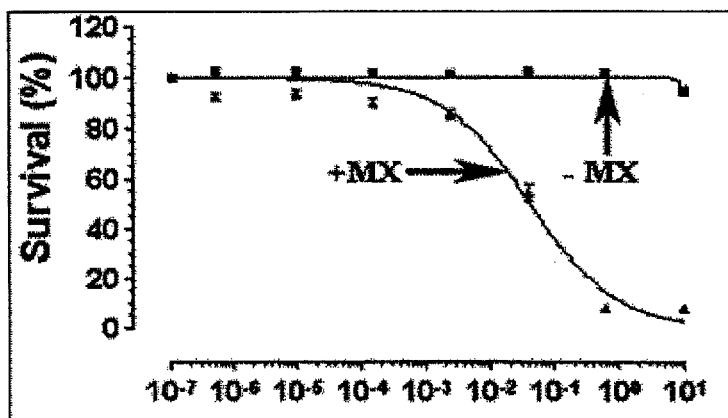
FIG. 13A. Graph illustrating the effect of varying the concentration of PZ-38 on the percent survival of HEK293/ABCG2 cells. The cells were treated without (■) or with 0.1 μM mitoxantrone ($IC_{10}$, ▲).
Figure 13B:
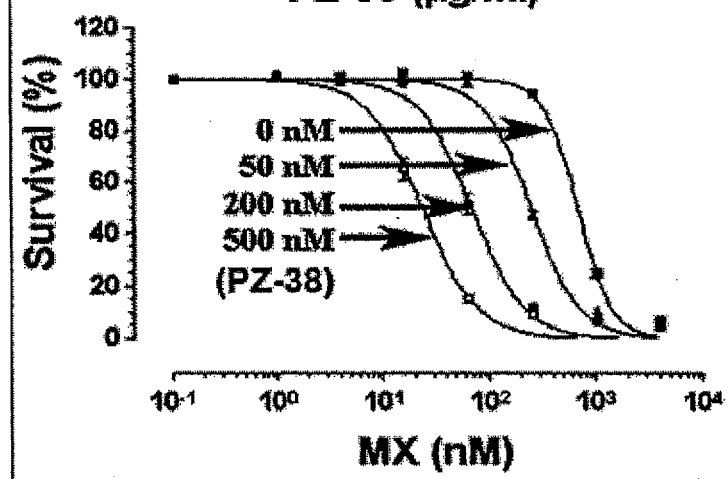
FIG. 13B. Graph illustrating the effect of varying the concentration of MX on the percent survival of HEK293/ABCG2, measured using different concentration of PZ-38 (▲, 50 nM; ●, 200 nM; Y, 500 nM) or the vehicle (0.1% DMSO, ■). The data are representative of four independent experiments.

Referring now to FIG. 13A, to test the inhibitory activity of PZ-38 on ABCG2 function, the concentration-dependent effects of PZ-38 on mitoxantrone cytotoxicity in ABCG2 transfected cells was also evaluated. Cell survival of HEK293/ABCG2 cells was measured in the absence (■) or presence (▲) of 0.1 µM mitoxantrone which alone produced less than 10% inhibition of cell growth. Compound PZ-38 was not cytotoxic at concentrations up to 10 µg/ml but it could sensitize cells to mitoxantrone at this concentration. The $IC_{50}$ of PZ-38 to sensitize mitoxantrone resistance is about 45 nM. Interestingly, the $IC_{50}$ of FTC to sensitize mitoxantrone resistance was 326 nM as previously determined, suggesting that PZ-38, similar to PZ-39, is more potent than FTC in sensitizing drug resistance. Because PZ-38 is less potent than FTC in inhibiting ABCG2-mediated drug efflux, the increased potency in survival assay may be due to its effect on ABCG2 stability. Referring now to FIG. 13B, we also measured the effect of varying the concentration of mitoxantrone on cell survival at different concentration of PZ-38, Graph illustrating the effect of varying the concentration of mitoxantrone on the percent survival of HEK293/ABCG2, measured using different concentration of PZ-38 (▲, 50 nM; ●, 200nM; Y, 500 nM) or the vehicle (0.1% DMSO, ■). The data are representative of four independent experiments.

Figure 14:
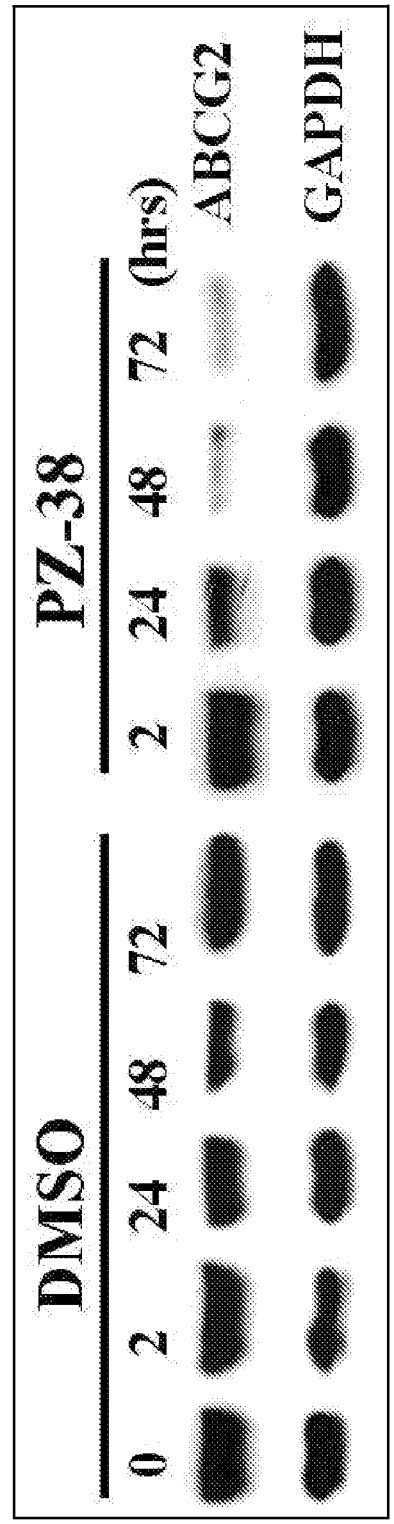
FIG. 14. Western blots illustrating the effect of either DMSO (left side) or PZ-38 (right side) on the levels of human ABCG2 in HEK293 cells over time. HEK293/ABCG2 cells were treated with 3.8 μM PZ-38 or DMSO control, and harvested at 0, 2, 24, 48 or 72 hours after exposure to PZ-38, GAPDH was used as a loading control.

Effect of PZ38 on human ABCG2, ABCB1 and ABCC1 expression level Referring now to FIG. 14, in order to determine if PZ-38 also acts on ABCG2 and contributes to its degradation in the cell similar to how PZ-39 acts, a western blot analysis of ABCG2 was conducted following treatment with PZ-38. The cells were sampled and tested for both ABCG2 (upper band) and GAPDH (lower band) at 0, 2, 24, 48 and 72 hours after exposure to either DMSO along (right side) or DMSO plus PZ-38 (left side). The levels of ABCG2 of decreased markedly following treatment with PZ-38 as compared to cell treated with only DMSO used as a control. Considering that PZ-39 causes lysosome-dependent degradation of ABCG2, it is likely that PZ-38 may have a similar mechanism of action on ABCG2. It was also found that PZ-38 has no effect on ABCB1 and ABCC1-mediated drug efflux (data not shown), suggesting that PZ-38 is likely specific to ABCG2.

Accessing the acute toxicity of certain ABCG2 inhibitors in mice. In order to detei mine the acute toxicity (lethal dose 50, LD-50) of the novel two-mode acting ABCG2 inhibitors, the compound C8 was tested to determine its effect on mice.

Briefly, BALB/c mice were inoculated with a single intraperitoneal injection of the compound at one of three dosages: 30 mg/kg, 10 mg/kg, or 3 mg/kg. The control animals received the solvent treatment. Within 1 week after injection with either the compound or a control comprising only the carrier the mice were observed twice daily for lethality. Results showed that five of eight mice died in 30 mg/kg group, and two of seven mice died in 10 mg/kg group, while all 6 mice survival in 3 mg/kg group. Based on the survival curves, the $LD_{50}$ of C8 for BALB/c was estimated to be about 22.5 mg kg$^{-1}$.

Figure 15:
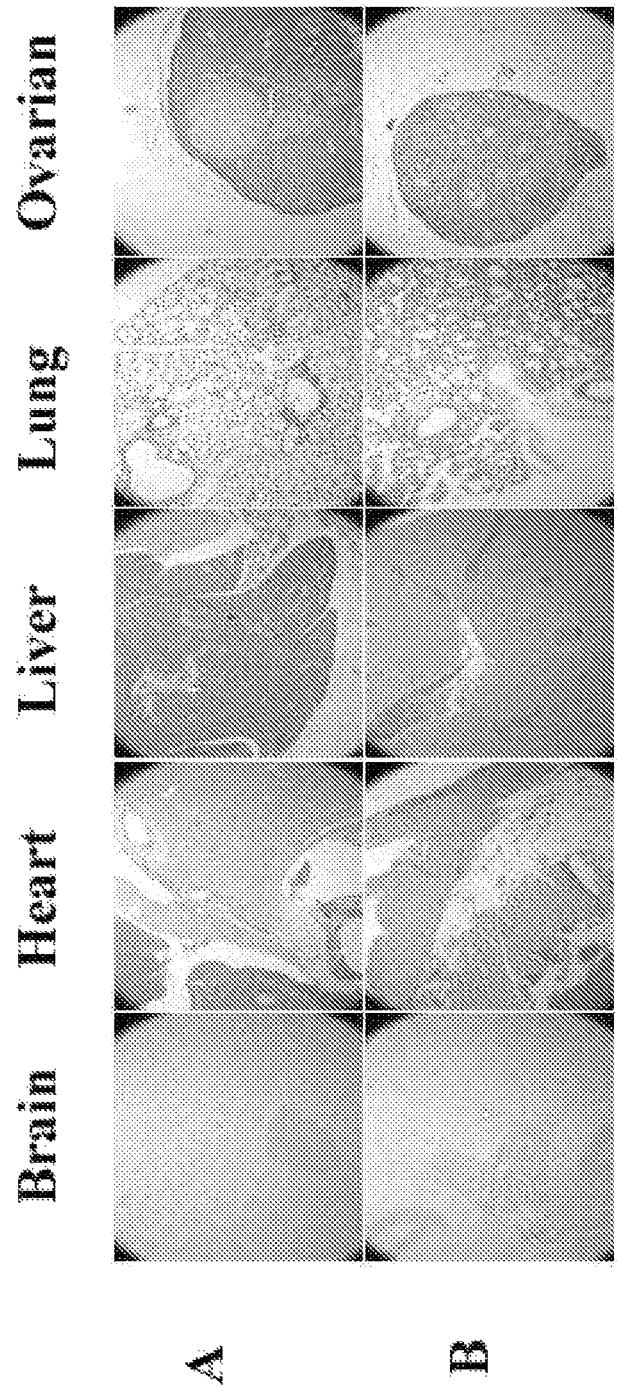
FIG. 15. Photomicrographs of tissue sample collected from mice treated with a lethal dose of compound C8.

Detection of C8-induced tissue injury by Histopathology testing. Referring now to FIG. 15, in order to further investigate whether C8 cause tissue injury, compound C8 was dissolved in formula number 1 (obtained from Pharmatek Laboratories, San Diego, Calif., USA) and BALB/c mice were injected intraperitonealy with a lethal dose 30 mg/kg of C8. On the day after the treatment, tissues including brain, heart, lung, liver, spleen, stomach, intestine, bladder, kidney, and ovarian were collected from the mice euthanized by carbon dioxide and fixed in the neutral formalin buffer immediately. For histopathological test, the paraffin embedded brain, heart, liver, lung, or ovarian tissue sections were stained with hematoxylin and eosine (H&E). Histopathological studies on treated tissue samples (FIG. 15 row B) of BALB/c mice demonstrated that there were no pathological changes, compared with normal tissues (FIG. 15 row A).

Figure 16:
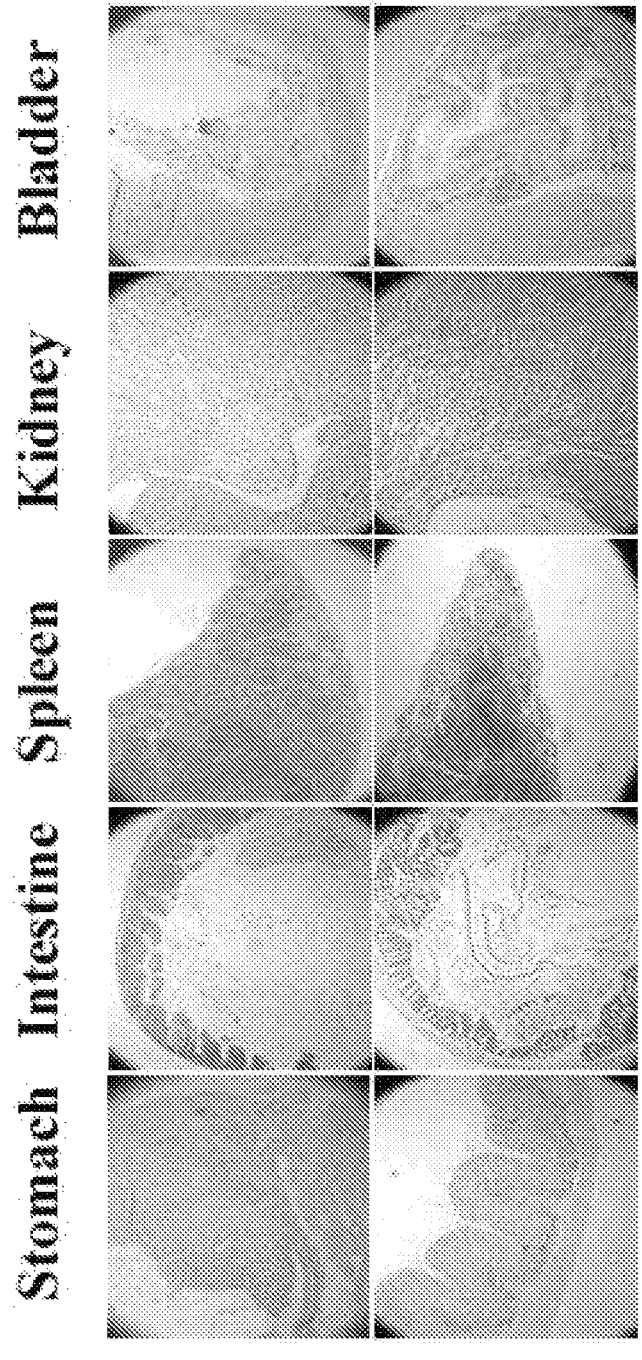
FIG. 16. Photomicrograph of tissue samples collected from mice treated with C-8.

Referring now to FIG. 16, photomicrographs of a Pathological study performed on C8-induced tissue damage that may have occurred in tissue collected from the animals stomach, intestine, spleen, kidney or bladder. H&E stained sections of control (FIG. 16 row A) and C8-treated (FIG. 16 row B). The images were collected at an original magnification of ×10). There were no pathologic changes in C8-inject mouse tissues as compared with normal tissues were evident.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. While the inventive technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

REFERENCES

1. Xu, J., Liu, Y., Yang, Y., Bates, S. & Zhang, J. T. Characterization of oligomeric human half-ABC transporter ATP-binding cassette G2. *J Biol Chem* 279, 19781-9 (2004).
2. Xu, J. et al. Oligomerization domain of the multi drug resistance-associated transporter ABCG2 and its dominant inhibitory activity. *Cancer Res* 67, 4373-81 (2007).
3. McDevitt, C. A. et al. Purification and 3D Structural Analysis of Oligomeric Human Multidrug Transporter ABCG2. *Structure* 14, 1623-32 (2006).
4. Zhang, J. T. Biochemistry and pharmacology of the human multi drug resistance gene product, ABCG2. *Zhong Nan Da Xue Xue Baa Yi Xue Ban* 32, 531-41 (2007).
5. Allen, J. D. et al. Potent and specific inhibition of the breast cancer resistance protein multidrug transporter in vitro and in mouse intestine by a novel analogue of fumitremorgin C. *Mol Cancer Ther* 1, 417-25 (2002).
6. Henrich, C. J. et al. A high-throughput cell-based assay for inhibitors of ABCG2 activity. *J Biomol Screen* 11, 176-83 (2006).
7. Henrich, C. J. et al. New inhibitors of ABCG2 identified by high-throughput screening. *Mol Cancer Ther* 6, 3271-8 (2007).
8. Ahmed-Belkacern, A. et al. Inhibitors of cancer cell multi drug resistance mediated by breast cancer resistance protein (BCRP/ABCG2). *Anticancer Drugs* 17, 239-43 (2006).
9. Xu, 1., Peng, H. & Zhang, 1. T. Human multidrug transporter ABCG2, a target for sensitizing drug resistance in cancer chemotherapy. *Curr Med Chem* 14, 689-701 (2007).
10. Ozvegy-Laczka, C. et al. Function-dependent conformational changes of the ABCG2 multi drug transporter modify its interaction with a monoclonal antibody on the cell surface. *J Bioi Chern* 280, 4219-27 (2005).

We claim:

1. A method of overcoming multidrug resistance in an individual undergoing cancer chemotherapy, the method comprising the step of:
providing to the individual a pharmaceutical composition comprising a chemotherapeutic reagent and an ABCG2 inhibitor, or a pharmaceutically acceptable salt thereof, wherein the ABCG2 inhibitor has a formula of:

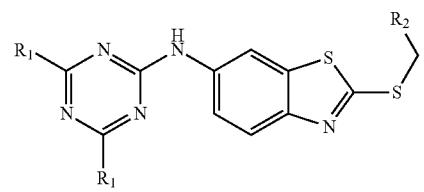

wherein $R_1$ is selected from the group consisting of:

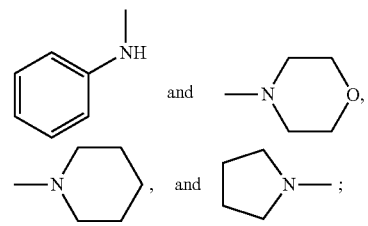

wherein $R_2$ is selected from the group consisting of:

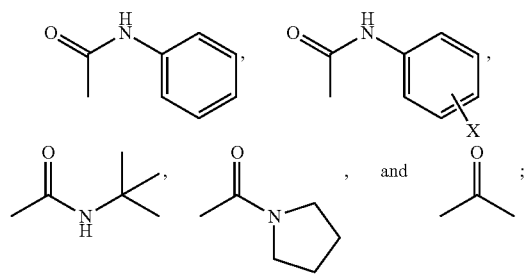

and
wherein X is a halide; wherein said chemotherapeutic reagent is selected from a group consisting of an anthracycline antibiotic, anthracenedione and topoisomerase I inhibitor.

2. The method of claim 1, wherein the ABCG2 inhibitor is present in the pharmaceutical composition at about 45 nM or less.

3. The method of claim 1, wherein the ABCG2 inhibitor is:

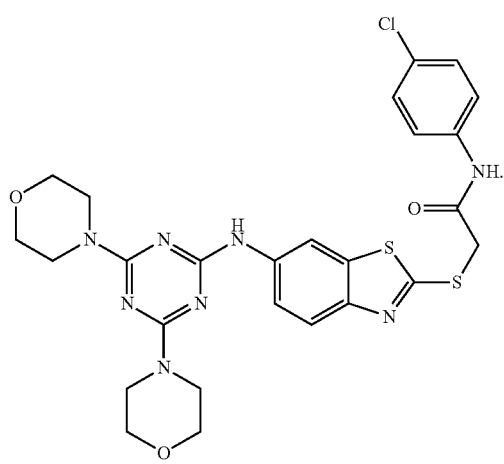 [SMILES: O=C(CSc1nc2ccc(Nc3nc(N4CCOCC4)nc(N4CCOCC4)n3)cc2s1)Nc1ccc(Cl)cc1]

4. The method of claim 1, wherein the ABCG2 inhibitor is:

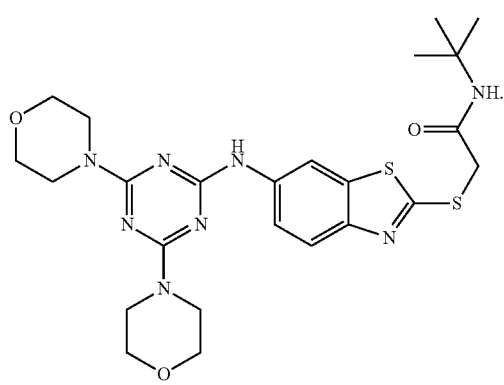 [SMILES: CC(C)(C)NC(=O)CSc1nc2ccc(Nc3nc(N4CCOCC4)nc(N4CCOCC4)n3)cc2s1]

5. The method of claim 1, wherein the ABCG2 inhibitor is:

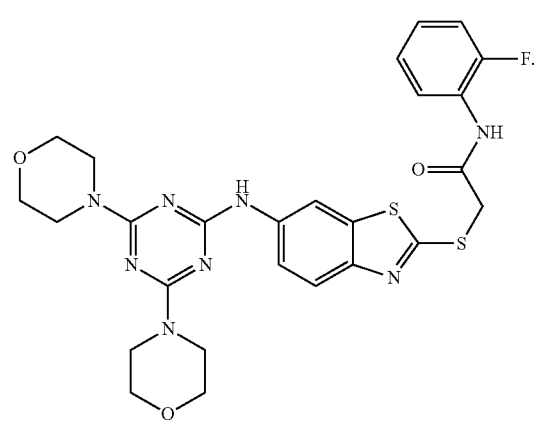 [SMILES: O=C(CSc1nc2ccc(Nc3nc(N4CCOCC4)nc(N4CCOCC4)n3)cc2s1)Nc1ccccc1F]

6. The method of claim 1, wherein the ABCG2 inhibitor is:

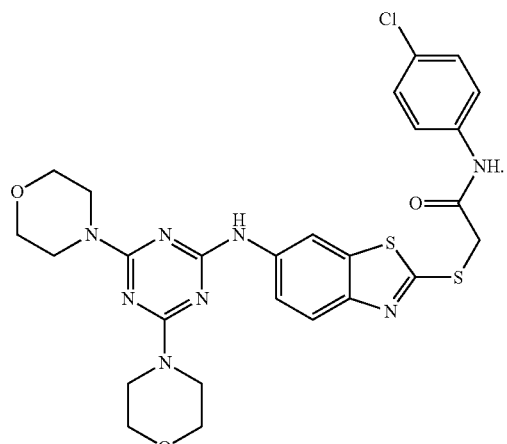

7. The method of claim 1, wherein the ABCG2 inhibitor is:

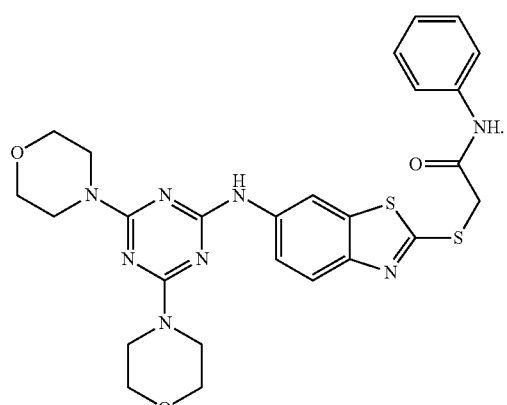

8. The method of claim 1, wherein the ABCG2 inhibitor is:

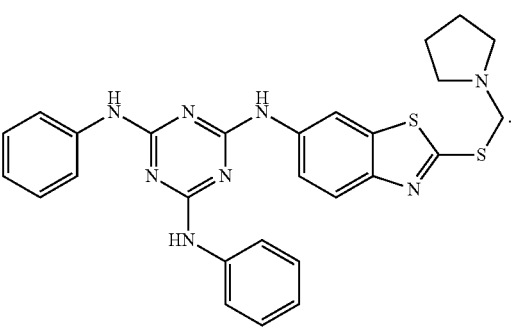 [SMILES: c1ccc(Nc2nc(Nc3ccccc3)nc(Nc3ccc4nc(SCN5CCCC5)sc4c3)n2)cc1]

9. The method of claim 1, wherein the anthracycline antibiotic is Adriamycin.

10. The method of claim 1, wherein the anthracenedione is mitoxantrone.

11. The method of claim 1, wherein the topoisomerase I inhibitor is topotecan.

12. The method of claim 1, wherein the topoisomerase I inhibitor is camptothecin.

* * * * *